(12) United States Patent
Avner

(10) Patent No.: US 6,520,639 B2
(45) Date of Patent: *Feb. 18, 2003

(54) DECORATIVE COVERS FOR MEDICAL EQUIPMENT

(76) Inventor: David B. Avner, 202 Garfield Ave., Liverpool, NY (US) 13088

(*) Notice: Subject to any disclaimer, the term of this patent is extended or adjusted under 35 U.S.C. 154(b) by 91 days.

This patent is subject to a terminal disclaimer.

(21) Appl. No.: 09/747,658

(22) Filed: Dec. 26, 2000

(65) Prior Publication Data

US 2001/0001188 A1 May 17, 2001

Related U.S. Application Data

(63) Continuation-in-part of application No. 09/200,134, filed on Nov. 25, 1998, now Pat. No. 6,165,035.
(60) Provisional application No. 60/066,812, filed on Nov. 26, 1997.

(51) Int. Cl.[7] .................................................. A61B 3/10
(52) U.S. Cl. ......................................... 351/205; 446/72
(58) Field of Search ................................. 351/200, 205; 446/71, 72, 73, 369, 370; 600/200, 504

(56) References Cited

U.S. PATENT DOCUMENTS

| 5,038,755 A | * | 8/1991 | Burgio et al. ............... 600/200 |
| 5,592,946 A | | 1/1997 | Eddy |
| 6,095,647 A | * | 8/2000 | Cook .......................... 351/200 |

* cited by examiner

Primary Examiner—George Manuel
(74) Attorney, Agent, or Firm—George R. McGuire; Hancock & Estabrook, LLP

(57) ABSTRACT

An exterior covering for various types of medical equipment is disclosed to reduce some of the intimidation created by medical equipment. The covering is configured to receive the medical device and is shaped to portray an object, such as an animal, plant, vehicle, building, etc., and can include a removable figure. The cover has recesses and channels, such as a lens viewing channel, corresponding to the specific equipment to permit unobstructed use of the equipment. When the covering is for a stethoscope, the covering can extend along the ear tubes proximate the ear pieces, between the ear tubes and/or beyond the tubes. When used for a blood pressure cuff the covering is a sleeve that is dimensioned to receive an inflatable bladder, hook and loop materials to enable the cover to be secured to itself and a tube receiving hole to enable the bladder to be inflated.

8 Claims, 28 Drawing Sheets

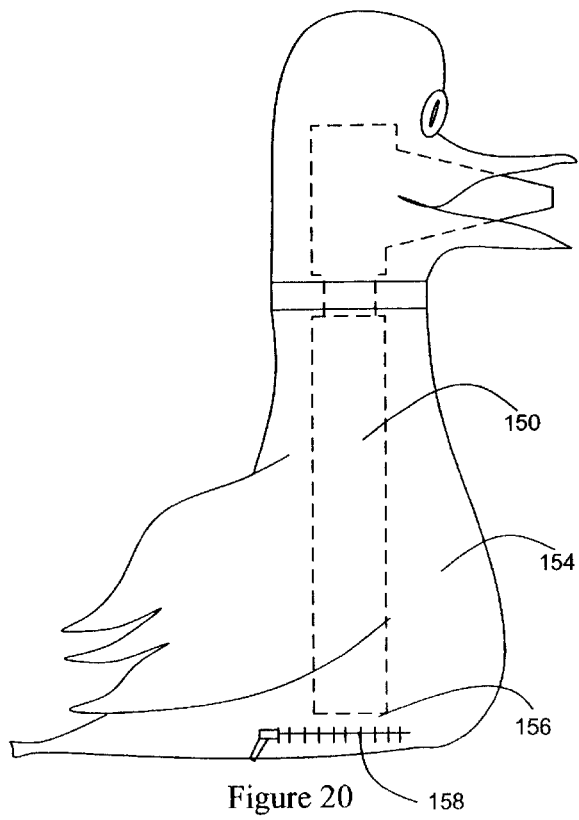
Figure 20
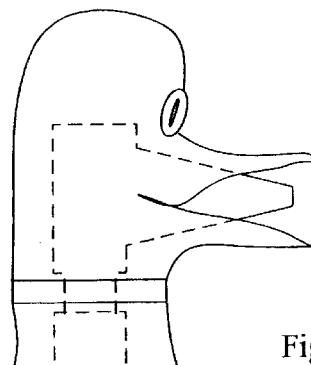
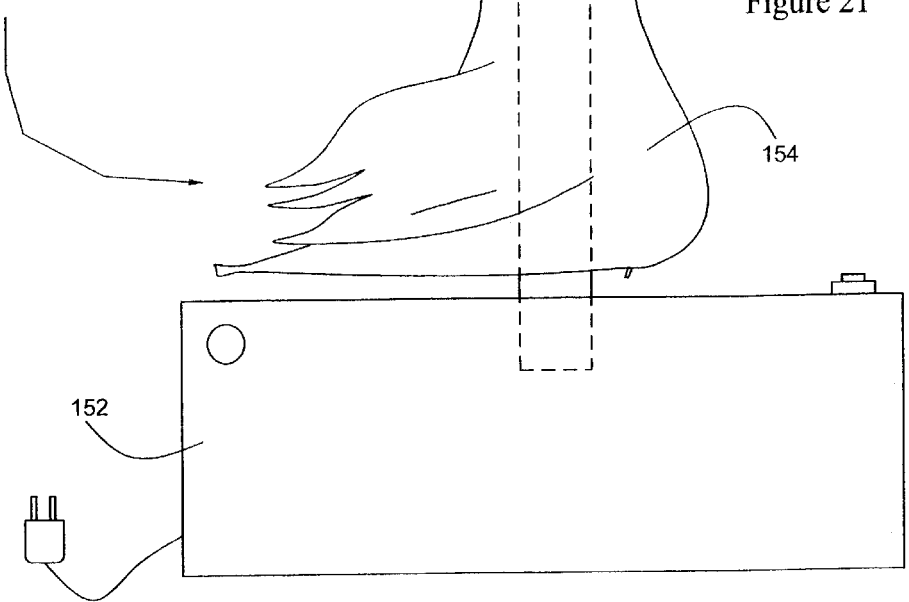
Figure 21

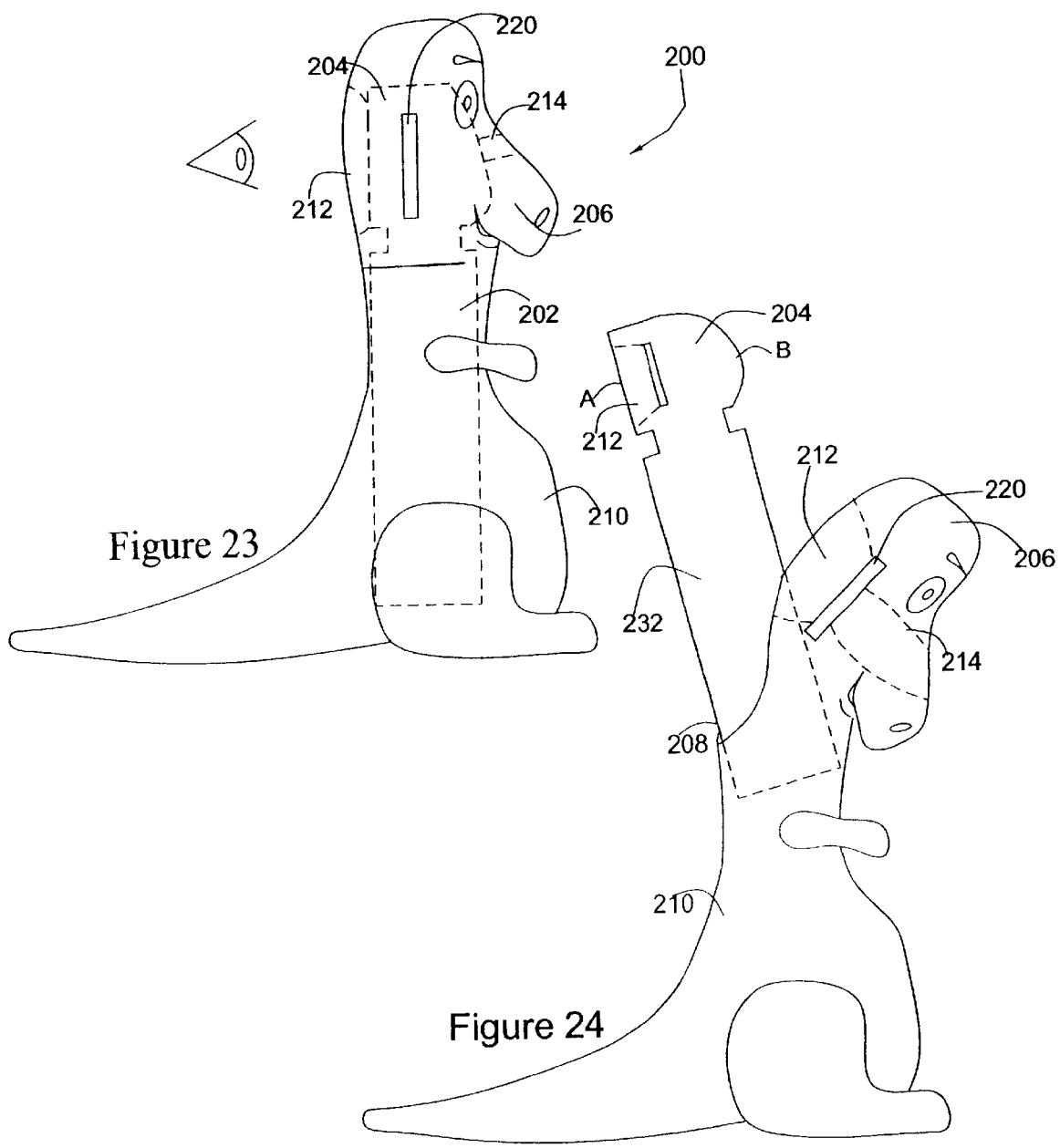

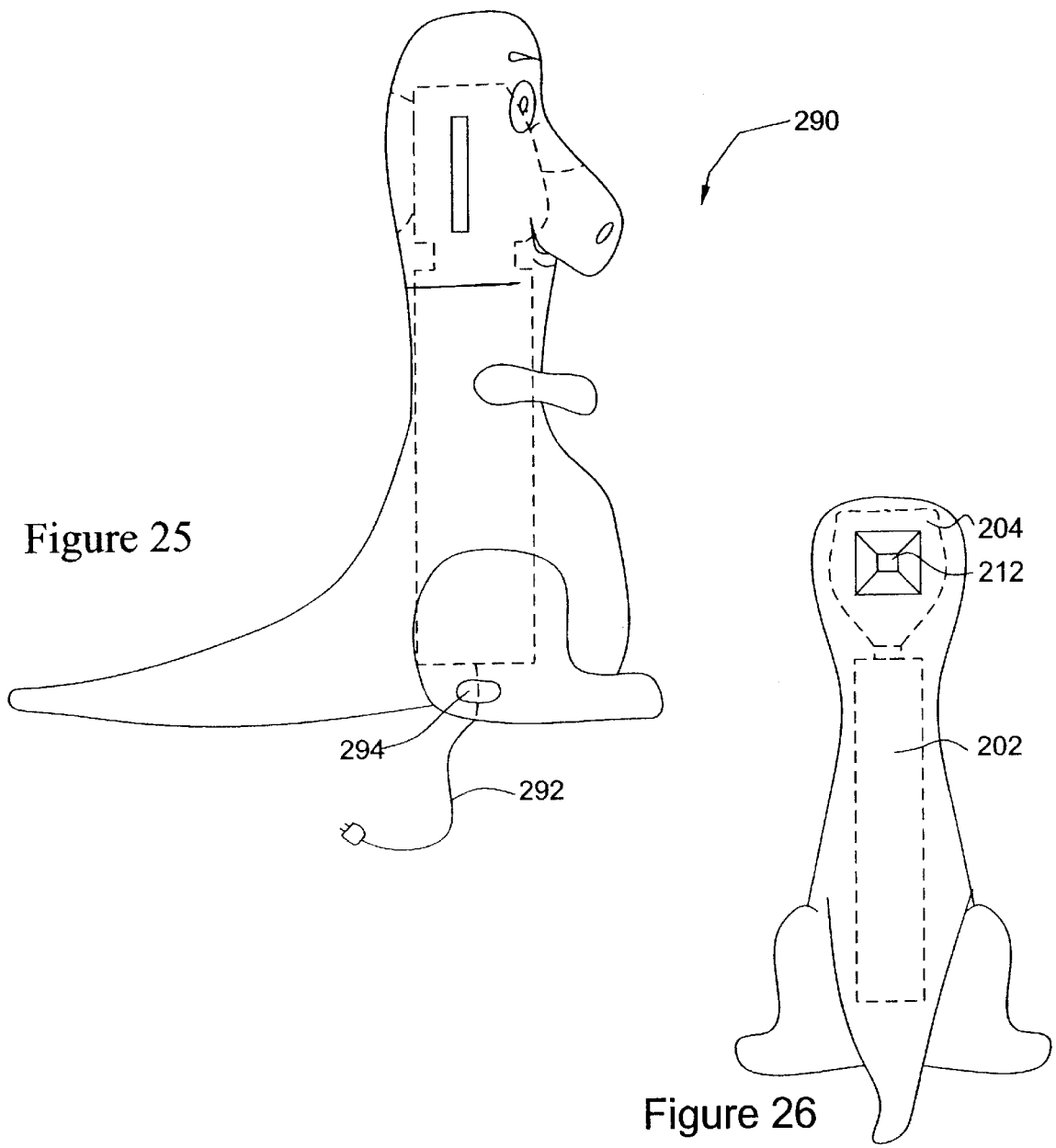

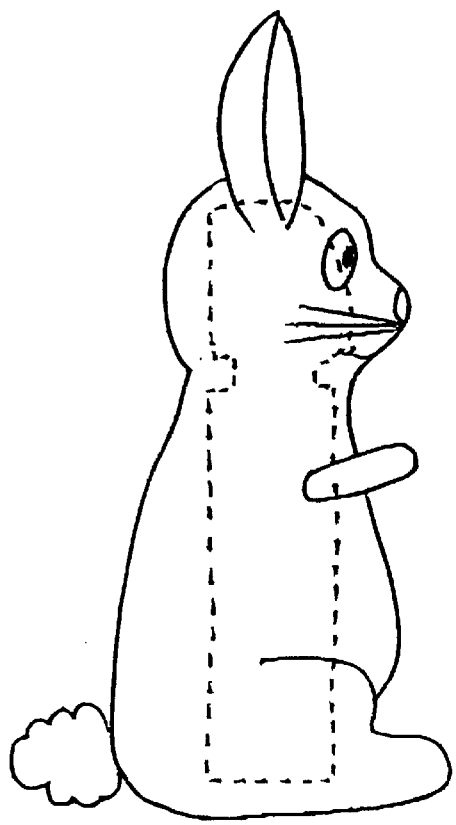
Figure 43
Figure 44
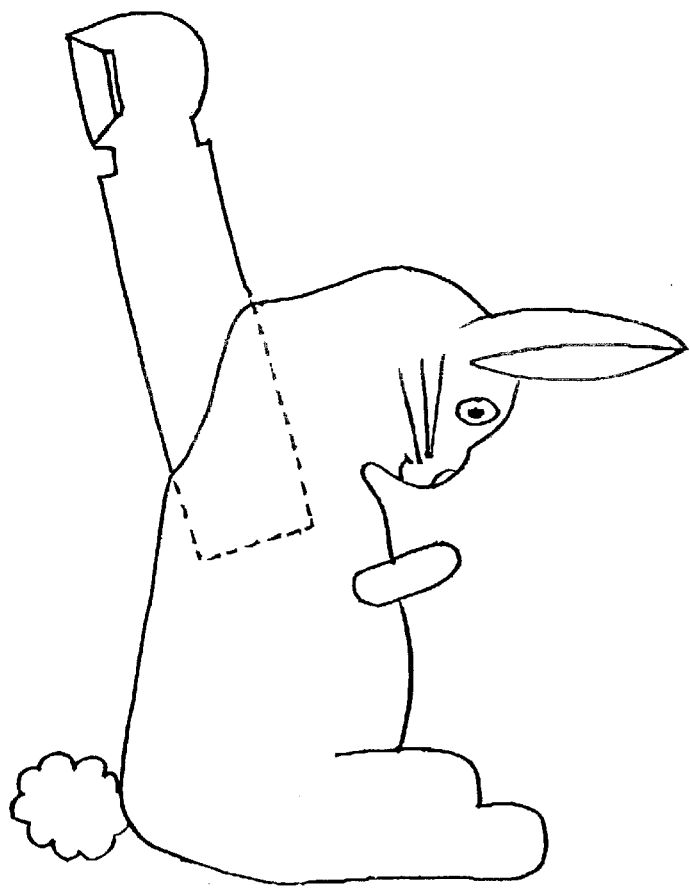

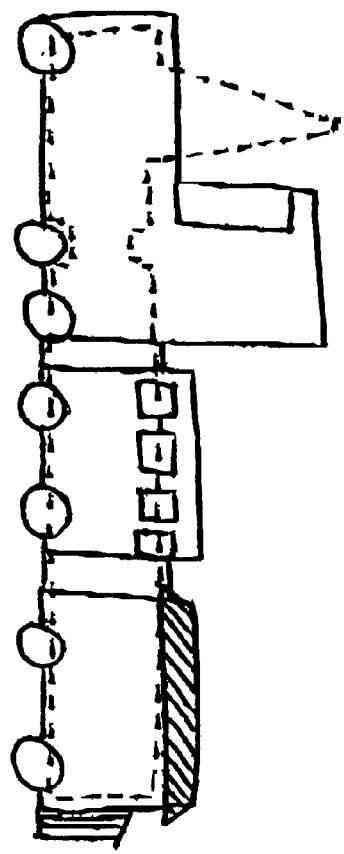
Figure 48
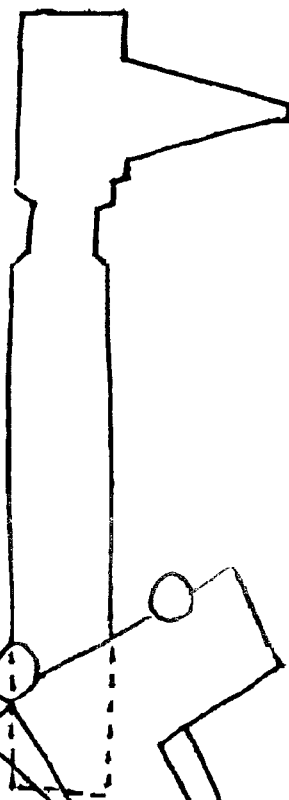
Figure 49
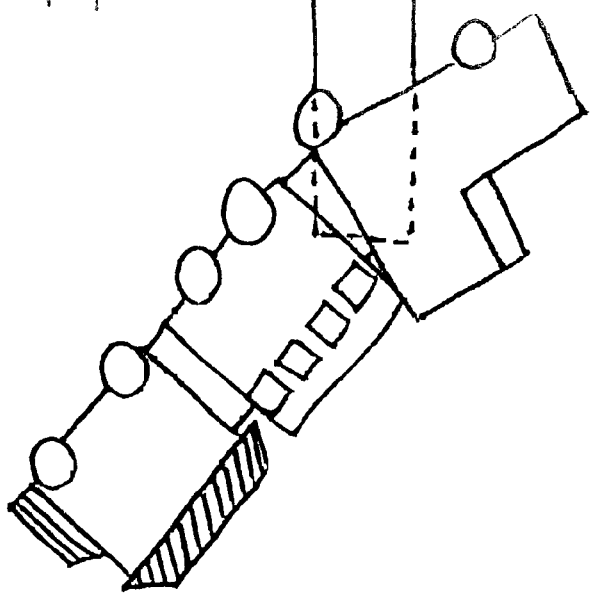

DECORATIVE COVERS FOR MEDICAL EQUIPMENT

CROSS-REFERENCE TO RELATED APPLICATION

This application is a continuation-in-part of copending patent application Ser. No. 09/200,134 filed Nov. 25, 1998, and claims the benefit of Provisional appl. No. 60/066812, filed Nov. 26, 1997. the disclosure of which is incorporated herein by reference, as though recited in full.

FIELD OF THE INVENTION

This invention relates to the production of a decorative covering, also referred to from here on out as a Pediapet, that will be used to cover or partly cover medical equipment in such a way that the equipment will appear less threatening to patients. In particular, this invention relates to the production of decorative covers in the shape of animals and other familiar objects that will be used to cover medical equipment such as stethoscopes, ophthalmoscopes, IV poles, crutches, blood pressure cuffs, syringes etc. and will help make the instrument or part of the instrument appear as though it is part of that animal or object.

BACKGROUND OF THE INVENTION

Visits to the hospital or doctor's office can be a scary and anxiety provoking experience for many patients, particularly in a pediatric setting. The fear and anxiety of being in a new surrounding, confronted by new faces and foreign instruments can stimulate a sympathetic nervous response in patients leading to such objective physical findings as increased heart rate, increased blood pressure, sweating, emotional liability, and changes in arterial blood gases. Most doctors find that it is advantageous to try to relieve these fears and anxieties before and throughout a physical exam or procedure. This allows the patient to feel more at ease during the exam which in turn gives the health care provider more accurate information about the patients health.

This had been recognized as a problem as problem and has been addressed in the prior art, such as U.S. Pat. No. 5,592,946 where they note that young patients are intimidated by the stethoscope. The '946 patent, however, primarily addresses the allergic reaction some health professionals have to the latex stethoscope tubing.

The disclosed medical instrument covers goes beyond any prior art covers by covering the instrument with a cover that makes it look like a familiar object, such as a stuffed animal. These covers are an easy way to distract and relax a young patient during a medical examination and/or procedure, making the instrument less threatening. Additionally, the covered instrument may be used to playfully distract a child during the exam and/or procedure.

SUMMARY OF THE INVENTION

The Pediapets are decorative covers in the shape of familiar objects such as animals, trees, clothing, etc. that are used to cover medical equipment that in turn is used during physical examinations and medical procedures. The covers are attached to the instrument in such a way as to give the medical instrument or part of the instrument the appearance of the object that the cover represents.

BRIEF DESCRIPTION OF DRAWINGS

FIG. 20 is a side view of a cover designed to accommodate an otoscopes that fits into a recharging rack;

FIG. 21 is a side view of the otoscope of FIG. 20 placed into the recharging rack;

FIG. 23 is a side view of a covered ophthalmoscope;

FIG. 24 is a side view of the ophthalmoscope being placed into the cover;

FIG. 25 is a side view of an additional cover for an electric ophthalmoscope including a hole to accommodate a cord;

FIG. 26 is a front view of the back of the ophthalmoscope illustrating the hole to accommodate the lens;

FIG. 43 is a side view of a covered ophthalmoscope showing a shroud that is a depiction of a rabbit-like structure;

FIG. 44 is a side view of an ophthalmoscope being placed into the cover of FIG. 43;

FIG. 48 is a side view of a covered otoscope showing a shroud that is a depiction of a train-like structure;

FIG. 49 is a side view of an otoscope being placed into the cover of FIG. 48;

DETAILED DESCRIPTION OF THE INVENTION

The disclosed covers are unique in that they are not merely figurines or decorative ornaments that have just been attached to the equipment, but rather are covers that are specially designed and fitted to cover a unique piece of medical equipment such as a stethoscope, crutches, otoscope, syringe, blood pressure cuff, etc. These playful covers help make medical examinations and procedures easier and more enjoyable for the patient and health care provider while helping to provide more accurate clinical information. In the embodiments directed to use of medical equipment, such as crutches or wheelchair, the uniqueness of the cover adds some fun while removing some of the intimidation of the equipment.

The following is a description of examples medical equipment covers, referred to generally as a Pediapet, that have been designed to cover several common medical examining instruments. The Pediapets illustrated depict predominately flora and fauna, however other designs, such as sporting equipment, stereo or recording equipment, etc., can be used. When appropriate to the final appearance and to provide more of a stuffed animal feel or sculpted appearance, stuffing can be inserted between the double layers of fabric. These designs are used herein as examples and other designs will become apparent to those in the art which can be used for these and other medical instruments and rehabilitation equipment. Other medical apparatus that is easily "converted" would be IV poles that look like coconut trees, with the IV as a "monkey" and the IV tube the monkey's tail. A pair of crutches could be covered to appear as a couple of tree trunks or flamingos, while a wheelchair can be covered to appear as a throne or some type of vehicle. Most any object can become a Pediapet as long as it has the overall exterior configuration of the medical apparatus. For example, it would be difficult to incorporate a ground hog onto a crutch. The physical structure of the crutch is such that it requires a long, relatively thin Pediapet, such as the flamingo or a monument. Conversely, the wheelchair would lend itself to the Lincoln monument, but would not make an especially good bird. Items of clothing can also be incorporated into the Pediapet design, such as the tie described hereinafter.

Cartoon characters especially lend themselves to becoming a Pediapet. Not only are they easy to reproduce as a three dimensional character, but they represent a certain level of familiarity, especially children. Other examples will become obvious to someone skilled in the art in conjunction with the instant disclosure.

STETHOSCOPE

Figure 1:
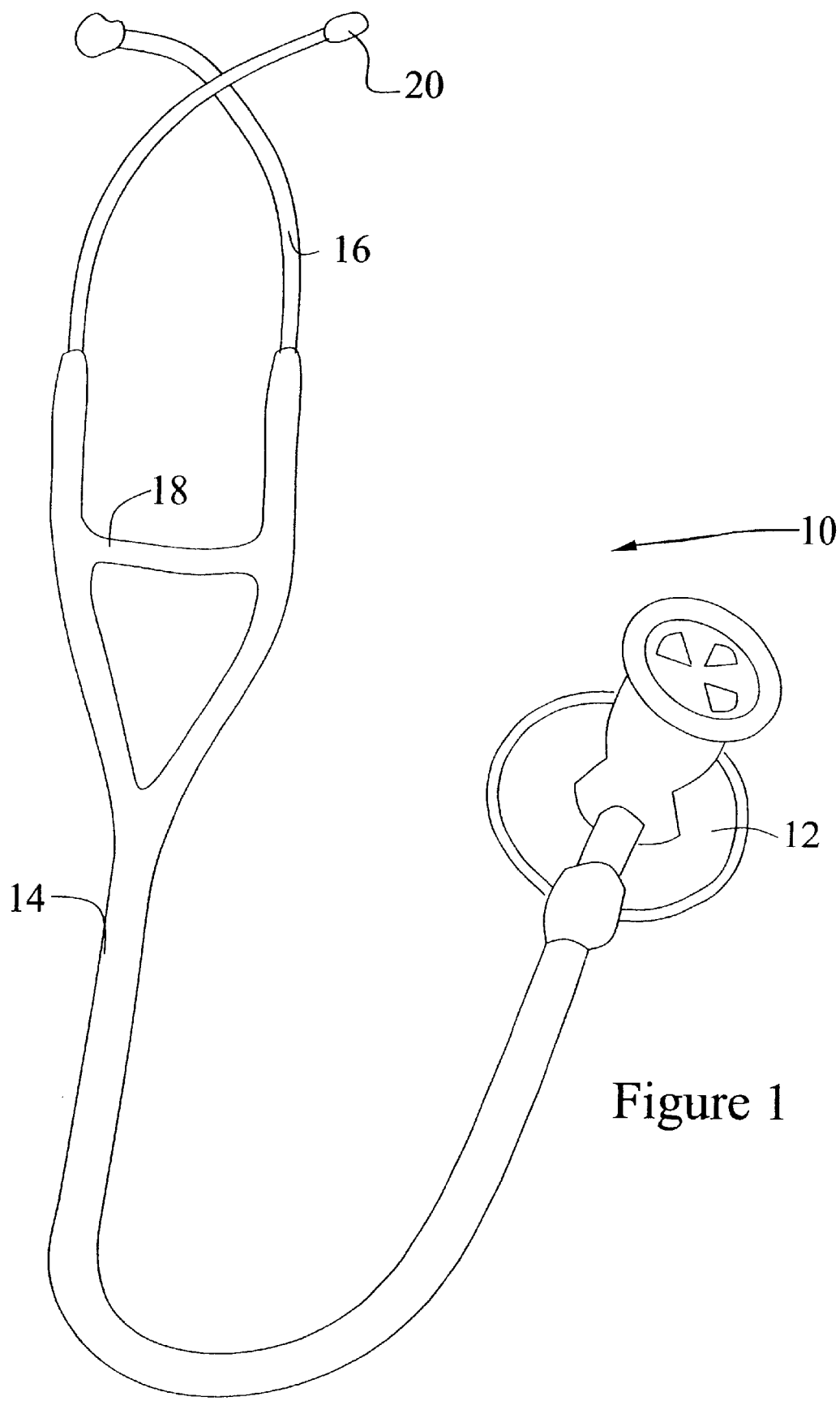
FIG. 1 is a perspective view of a standard stethoscope.

The stethoscope 10, illustrated in FIG. 1, is a listening equipment used to amplify sounds originating from within a living body. Its design consists of a head 12, comprising a bell and diaphragm, a flexible connective tube 14 of varying length to conduct sound from the head 12 of the stethoscope 10 to the headset 16, and a headset 16 which conducts sound from the flexible connective tube 14 to the listener's ears. The headset 16 consists of two metal tubes connected at a "Y" spring joint. Soft ear pieces 20 are connected to the end of each metal tube.

Figure 2:
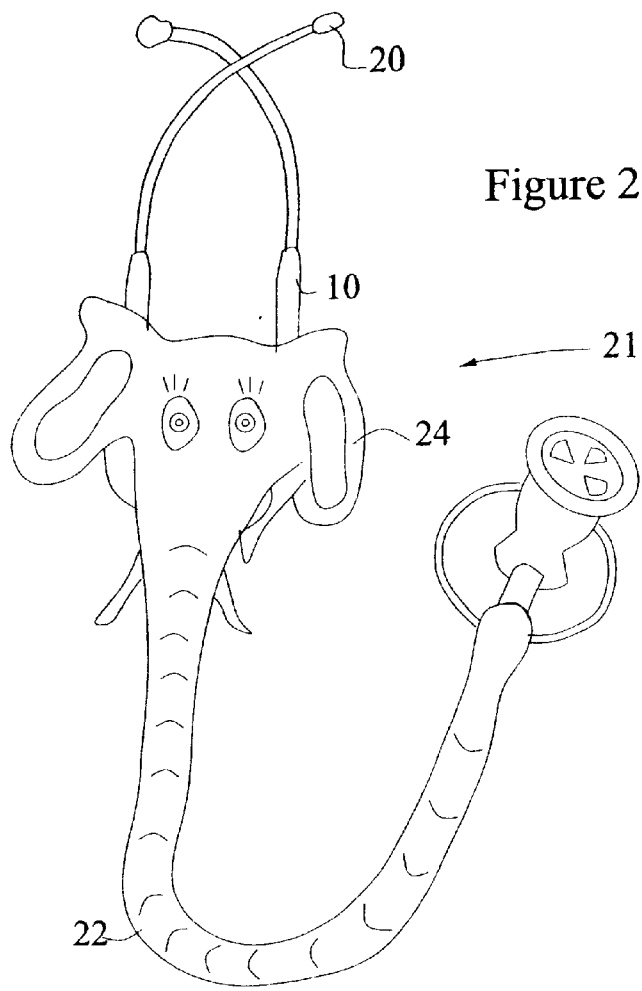
FIG. 2 is a front view of a stethoscope cover taking the form of an elephant.

The Pediapet is uniquely designed to fit the contours and shape of the stethoscope 10 without hindering its function and utility. FIGS. 2, 3, 4 and 5 illustrate examples of the shape of the covers which can be applicable. The elephant 21, illustrated in FIG. 2, is ideal for use with the stethoscope 10 as the trunk shaped sleeve 22 of the elephant 21 provides a natural cover for the connective tube 14 of the stethoscope 10. The ears and head, forming the body 24 of the cover also provide for an optimal aesthetic flow along the widest part of the headset 16. Due to its applicability, the attachment methods described herein will be directed to the elephant 21, however the various methods for attachment described hereinafter can be incorporated with any Pediapet embodiment.

Figure 3:
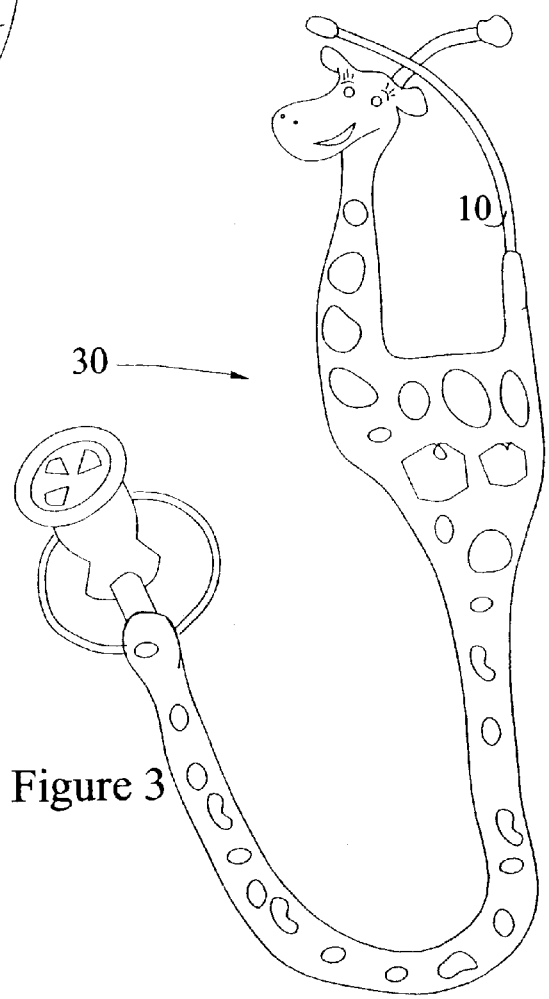
FIG. 3 is a front view of a stethoscope cover in the form of a giraffe.
Figure 4:
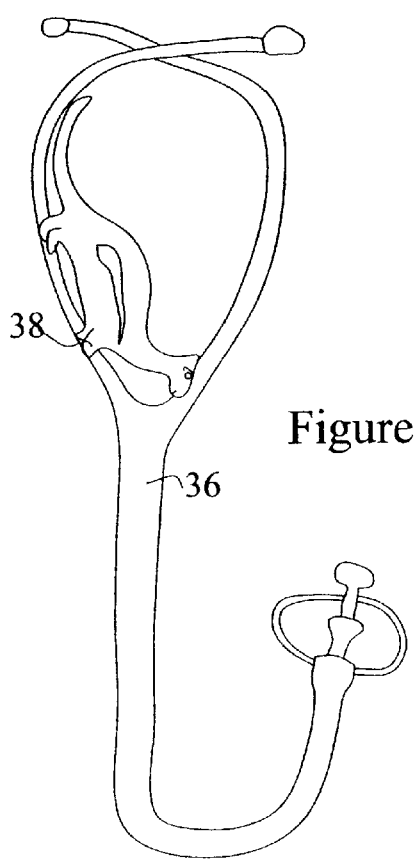
FIG. 4 is a front view of a stethoscope having an animal placed on the Y shaped tubes.
Figure 5:
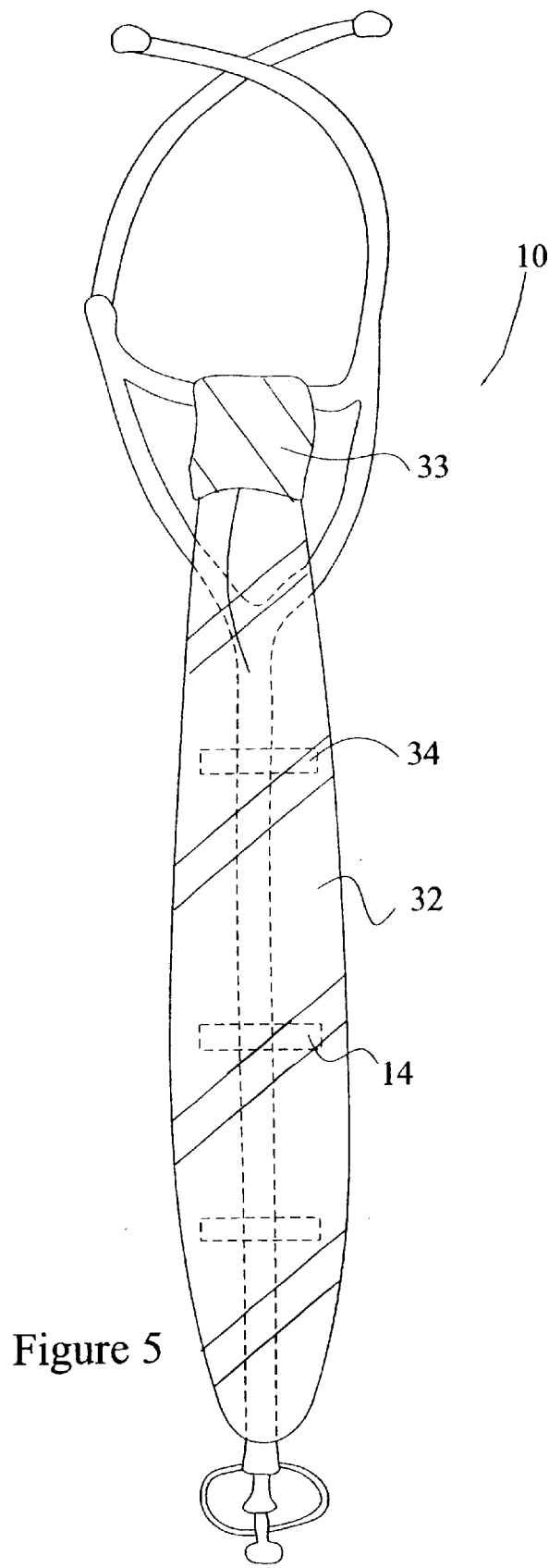
FIG. 5 is a front view of a man's tie covering for use with a stethoscope.

In FIG. 3 a giraffe 30 is used to cover the stethoscope 10, with the head extending along one of the connective tubes 14 and the tail extending partially along the other tube 14. The legs of the giraffe 30 are, as with all 4 legged animals, "consolidated" into one "leg" to fit with the configuration of the stethoscope 10. In FIG. 4 the cover is a snug fitting cover 36 which can represent a tree branch or other inanimate object. One or more small animals 38 are then attached, either permanently or removably, to the cover 36. The removable animal 38 is advantageous in that it can be given to the patient to play with during the examination. In FIG. 5 the stethoscope 10 is covered with a cover resembling a neck tie 32 which widens along the length and then comes to a taper at the end. For aesthetics the necktie 32 is manufactured to appear as though it has a knot at the neck. In the optimum embodiment, the necktie 32 is affixed to the stethoscope mid-bar 18 through use of hook and loop material 33 or other means known in the art. The tie 32 is attached to the connective tube 14 through use of tabs 34.

In its ideal form, the instrument cover consists of a soft sleeve into which the above mentioned parts of the stethoscope 10 can be inserted. The sleeve is designed to conform to the shape of the stethoscope so that part of the sleeve fits around the listening tube and head of the stethoscope, and part of the sleeve fits around the headset. The sleeve is made of a single and/or double layer of fabric that surrounds part or the entirety of the instrument. Different amounts of stuffing are placed between the double layer of fabric to further define the desired appearance of the animal or object being represented. Those parts of the cover that are stuffed can be stuffed either all the way around the circumference of the sleeve or partially around the circumference enabling a variation in how flat the stethoscope rests against the user.

Using the elephant of FIG. 2 as an example, the portion of the sleeve 22 containing the connective tube 14 and head 12 of the stethoscope 10 is manufactured with sufficient width to allow the diaphragm portion of the head 12 to pass through the length of the sleeve 22 to the listening end open end. Since the width of the diaphragm varies from one brand of stethoscope to another, the inner diameter of this part of the sleeve must is at least 3–6 cm.

Figure 10:
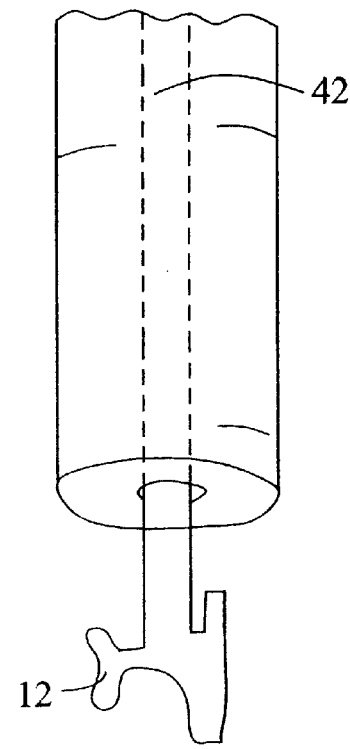
FIG. 10 is a perspective view of another embodiment of covering the bell/diaphragm end of the cover with the bell/diaphragm extending beyond the cover.
Figure 11:
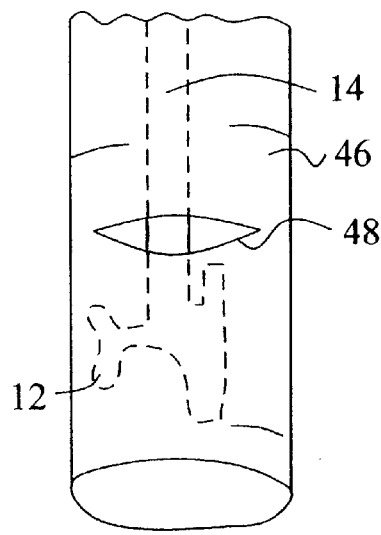
FIG. 11 is a perspective view of an additional embodiment of covering the bell/diaphragm with a slit being provided for the bell/diaphragm.
Figure 12:
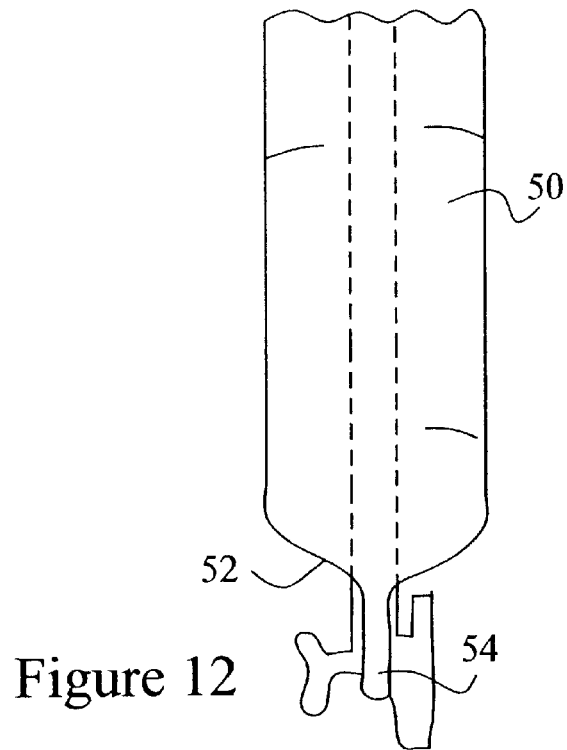
FIG. 12 is a perspective view of an alternative embodiment of covering the bell/diaphragm wherein the end of the cover is attached to the bell/diaphragm.

To prevent interference with the acoustics, it is critical that in all embodiments the end of the sleeve has an opening with a sufficient size to allow the stethoscope head to be exposed, allowing direct contact with the patient. More detailed examples of the ratio between the sleeve and the head 12 of the stethoscope are illustrated in FIGS. 9–12. In the embodiment of FIG. 10, the head 12 is always exposed through an opening at the end of the sleeve 42 and is always directly accessible. In the embodiment illustrated in FIG. 9, the sleeve 45 is longer than the length of the connective tube 14 and extends over the head 12. Therefore, the head 12 is not exposed until the sleeve 45 is pulled back to reveal the manufactured opening 44. Alternatively, the length of the sleeve can be less than the length of the connective tube and the head enclosed by a swatch of fabric folded over and secured by a snap, hook and loop material, etc. Additionally, any of the embodiments herein can have a closure system, such as hook and loop material. In the embodiment of FIG. 11 the opening 48 is placed along the length of the sleeve 46 proximate the head 12. To access the head 12, the head 12 is pulled through the opening 48 and the sleeve 46 pulled to one side. Since the surface area of the head 12 varies from one instrument to another the openings disclosed must be at least about 3–6 cm in diameter. In the design of FIG. 12, the open end 52 of the sleeve 50 is separated at approximately the middle, by a stirrup 54 of cloth or other material, which allows both the bell and diaphragm to be exposed simultaneously. The diameter of the openings are made wide enough for the entire surface of the bell and diaphragm to make contact with the patient.

Figure 6:
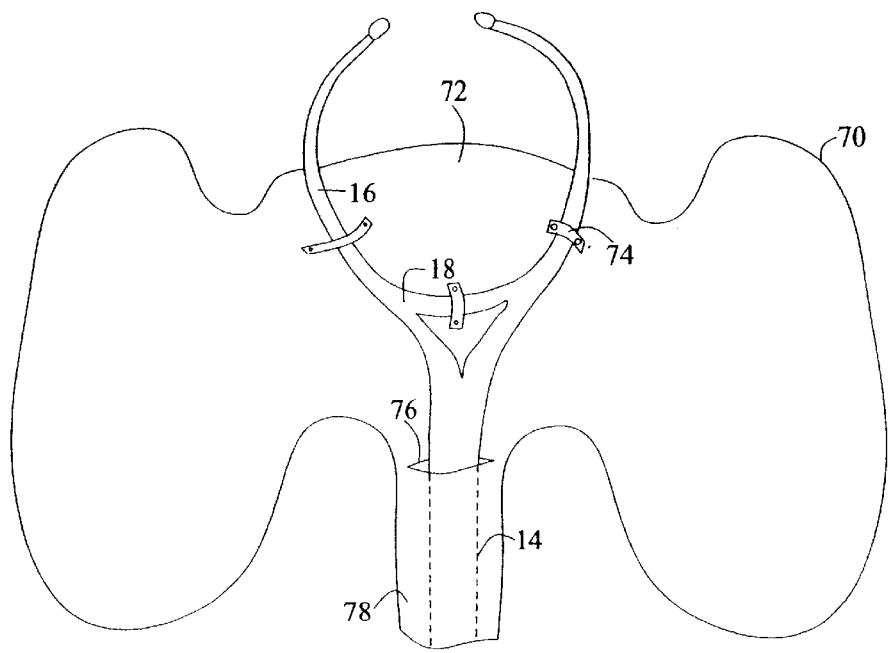
FIG. 6 is a front view of the back of the elephant illustrating the attachment method.
Figure 7:
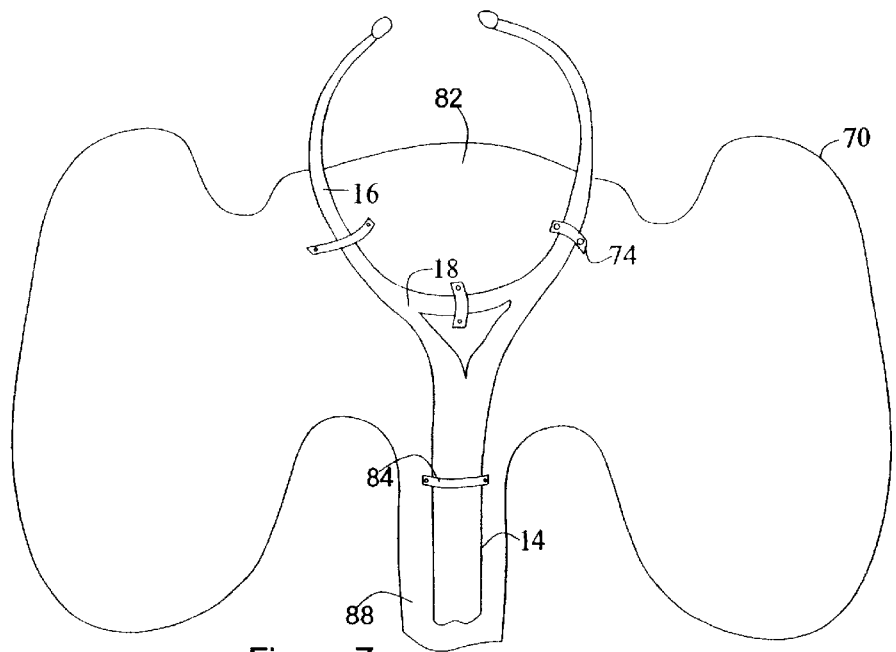
FIG. 7 is a front view of the back of the of the elephant illustrating an alternate attachment method.
Figure 8:
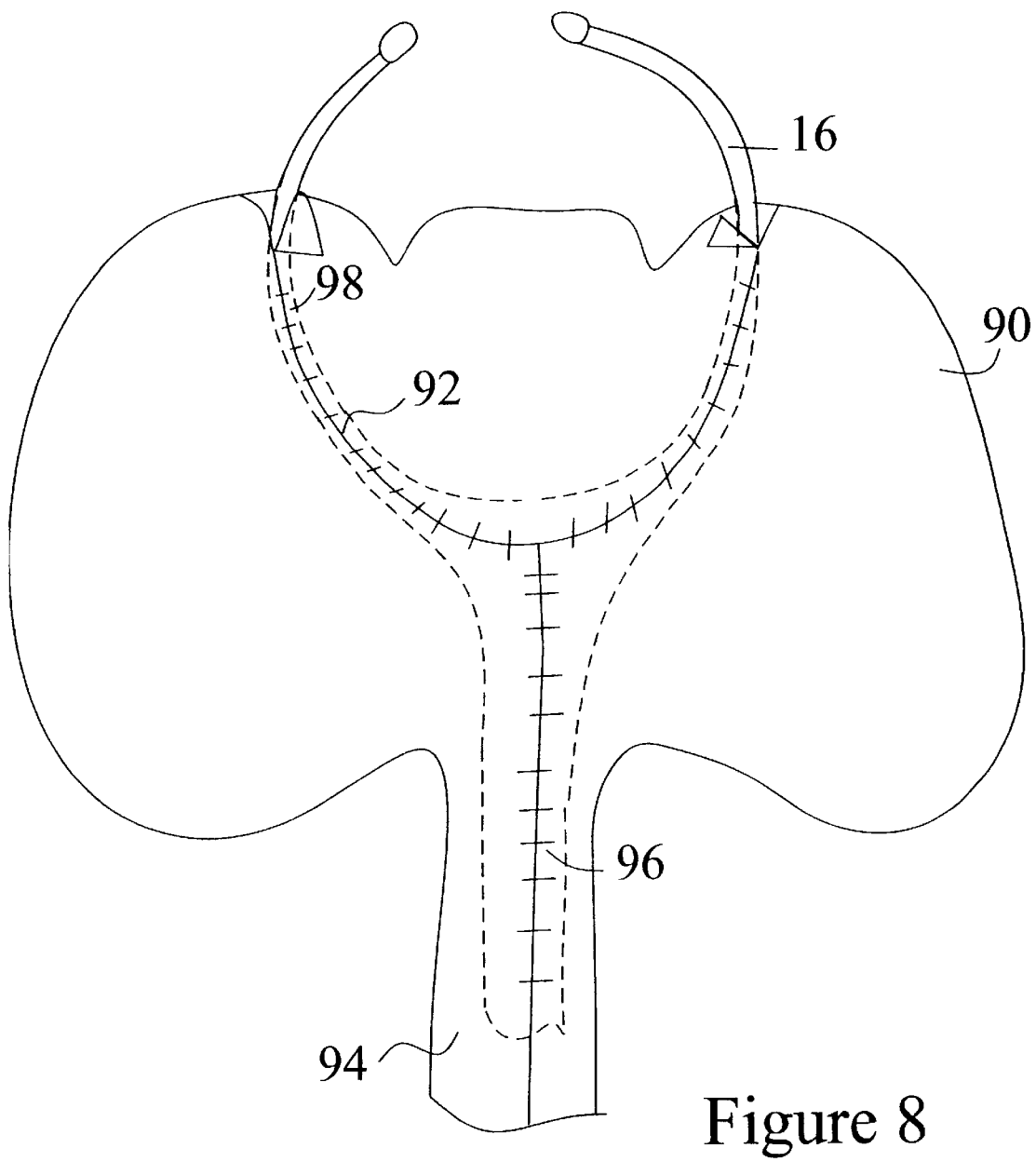
FIG. 8 is a front view of the back of the of the elephant illustrating an additional attachment method.

In FIGS. 6, 7 and 8, the back of the elephant 21 illustrates the various methods of connecting the cover and the stethoscope 10. In FIG. 6 the elephant 70 has a slit 76 which allows the connective tube 14 to be placed within the trunk 78. The slit 76 must be at least 5–7 cm in width to allow the diaphragm of the head and the neck of the headset to pass into the sleeve 78. In this, as well as other embodiments wherein the connective tube 14 is placed within the sleeve, the sleeve must be of double layers of material, there requiring an increase in the outer dimensions of the sleeve. The headset 16 is maintained in position at the back of the cover body 72 through use of tabs 74. These tabs 74 can be snaps, hook and loop, or other connective means which enables the stethoscope 10 to be removed from the cover. The tabs 74 are placed not only to prevent the body 72 of the cover from flopping forward but should provide sufficient stability to prevent a child from easily dislodging the body 72 from the headset 16. In FIG. 7 the stethoscope 10 is affixed to the back of the body 82 and sleeve 88 of the elephant 80 through the use of tabs 84 as noted above. In this embodiment, however, the connective tube 14 does not slide into the sleeve 88, but rather lies adjacent the exterior of the sleeve 88. The connective tube 14 is retained adjacent the sleeve 88 through use of tabs 84 placed along the length.

In FIG. 8 the body 90 is designed to receive the stethoscope 10 within the full sleeve 94 formed from the fabric layers. The closure line 92 is designed to open to receive the headset 16 and connective tube 14 and then close, securing the stethoscope 10. The closure line 92 can be any closure means, such hook and loop, zipper, snaps, which can be repeatedly opened and closed. Since the headset is forked like a wishbone, the full sleeve 94 is also forked like a wishbone. The headset portion 98 of the sleeve 94 accommodates the metal tubes and, since the metal tubes are not as wide as the diaphragm of the stethoscope, the headset portion 98 only requires a minimum interior diameter of about 0.5 to 3 cm. Each end of the wishbone corresponds to the metal headset tubes and has an opening at the end, at least 0.5 cm, to permit the earpieces to pass through. In this embodiment, the closure line 92 opens to accommodate the connective tube, therefore enabling the diameter of the connective tube portion 96 to approximately equal to the headset portion 98. In embodiments where the closure line 92 only opens to accommodate the headset 16, the connective tube portion 96 must have an interior diameter sufficient to accommodate the head 12.

It must be noted that when attaching the stethoscope 10 to the back of any of the Pediapets, the need to expand the headsets 16 to accommodate the user must be taken into account. This becomes more critical as the Pediapet is placed closer to the ear pieces 20 and care must be taken to properly position the headsets 16 at the time of making the patterns. Since the item portrayed should be expanded fully during use, the tabs 34 or closure line 92 are positioned to maintain the headsets 16 in an "in use" position, causing the Pediapet to be slightly folded when in the closed positions illustrated in FIG. 1. The Pediapet can also be placed lower on the headsets 16, closer to the mid-bar 18, allowing for the required headset 16 flexibility to be above the restraints created by either the tabs 34 or the closure line 92.

An alternative method of inserting the stethoscope is to have the head and flexible listening tube pass into the instrument cover from an opening in the sleeve corresponding to the neck of the headset much in the same way that a foot would pass into a sock. With this construction a fastening equipment is designed to pass over the neck of the headset and latch the sleeve in place; this prevents the sleeve from sliding off the end of the instrument. Other designs contain a combination of the above mentioned insertion options. These designs allow for some parts of the stethoscope to slide into the sleeve while other parts of the stethoscope have the sleeve wrapped around it.

The decorative covers for the stethoscope are not limited to the sleeve design. The covers are also manufactured to cover just the front of the stethoscope. Like the sleeve design, these covers are specifically designed to follow the contour of the stethoscope and allow for complete function and utility of the instrument. The covers that attach to the front of the stethoscope consist of a couple layers of fabric or other manufactured material that are cut out, sewn together, and stuffed to look like an animal or some other familiar object. The cover is then secured to the stethoscope with fastening devices specially designed to wrap around the head, the flexible listening tube, the neck of the headset, and/or the metal headset tubes of the stethoscope to prevent it from falling off.

In the event sporting equipment is preferred over animals, the stethoscope can be designed as a golf bag containing golf clubs. The ear tubes would be two of the golf clubs while the base tube would be "hidden" in the golf bag. Decorative material can also be added to the Pediapet cover that aids in the artistic representation of the object or animal the cover represents.

Otoscope

Figure 14:
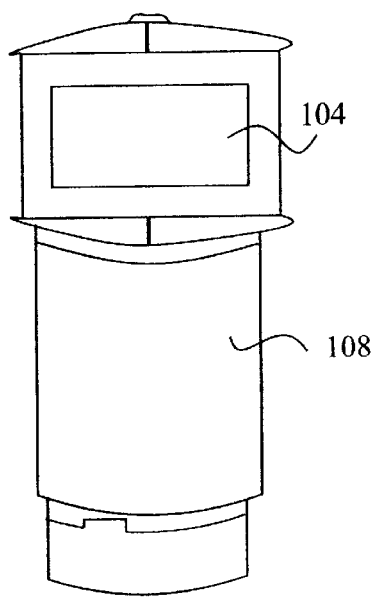
FIG. 14 is a front view of the detached head of the otoscope.
Figure 13:
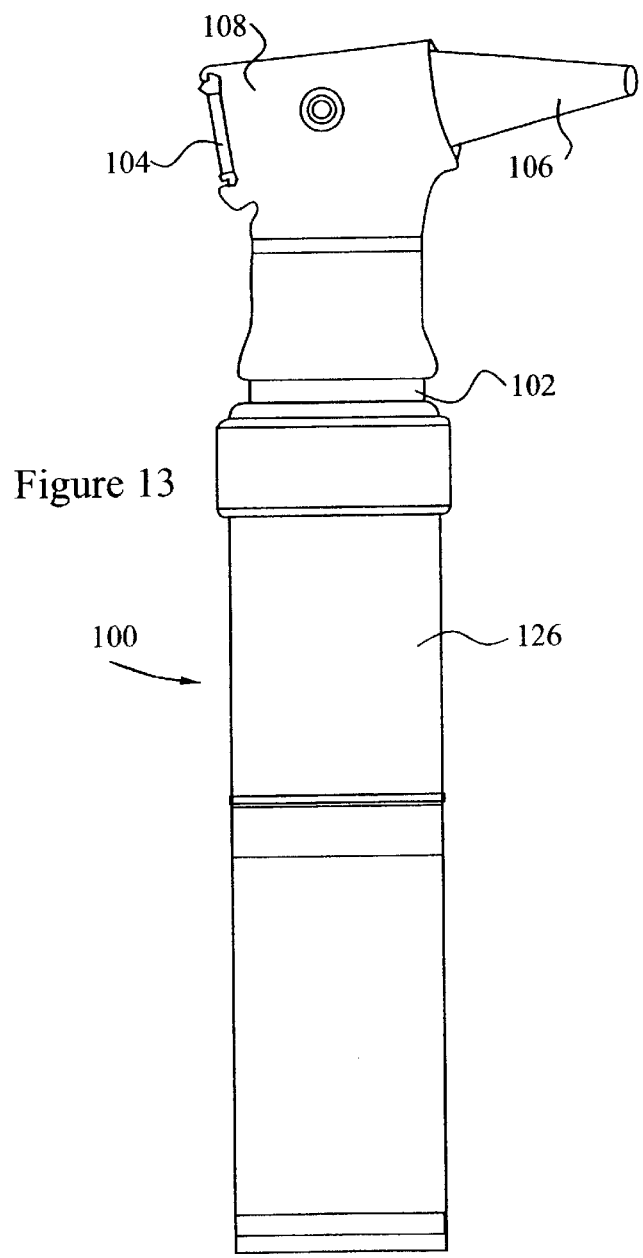
FIG. 13 is a side view of an assembled otoscope.

The otoscope 100, illustrated in FIGS. 13 and 14, is a medical instrument principally used to examine a patient's ears, nose, throat, and sinuses. It consists of a handle 126 that can contain a power source and a detachable head 108 that houses an illumination source and optic pieces 104 and provides a place for the attachment of a speculum 106. The handle 126 and head 108 attach at the neck of the otoscope 100. Portable otoscopes 100 are turned off and on by a button and rotating cuff 102 located at the junction of the handle 126 and head 108 of the otoscope. This cuff 102 also controls the brightness of the light.

Some otoscopes turn on automatically when they are removed from a holding rack that is usually mounted on a wall. These otoscopes are plugged into a power source and the electrical cord runs from the holding rack to the bottom of the handle of the otoscope. Still other otoscopes sit in a charging rack that makes contact with the instrument at the bottom of the handle. These otoscopes do not have a cord attached to them.

There are different sized otoscopes and there are slight variations in their shape depending on the company producing the instrument. This description of the Pediapet pertains to use with a standard sized portable otoscope. However, scaled down versions, and slight variations are made to the design of the Pediapet to cover other instrument sizes and accommodate mounting and recharging devices.

The Pediapet is designed to cover the handle 126 and/or the head 108 of the otoscope 100 while enabling full function and utility of the instrument. In its ideal form the otoscope Pediapet consists of a hollow sleeve 120 that is sealed at one end, such as illustrated in FIGS. 15–21. The sleeve 120 of the Pediapet is approximately 17 cm long, but varies slightly with model of the otoscope and the design of the animal or object it represents. The Pediapet is made to enable the otoscope 100 to slide in handle 126 first through an open end or slit 124 in the sleeve of the Pediapet.

This covers the handle 126 and, in some cases, part of the neck of the instrument. A specially designed hood 122 is attached to the sleeve and is pulled up over the head 108 of the otoscope. The hood 122, in the illustrated embodiment, is approximately 5.0 cm in length to enable the hood 122 to be easily placed over the otoscope head 108. In some cases, depending on size of the instrument and design of the Pediapet, the hood can also be an extension of the sleeve. Two holes are made in the hood 122 to permit examination of the patient. The viewer hole 128 is closest to the examiner's eye and generally has a periphery of at least about 2.5×3.0 cm and enables the viewer to look through the optic lens. The speculum hole 130 is opposite the first and is at least 0.5 cm in diameter to accommodate the speculum 106 attached to the head of the otoscope 100. The hood 122 must be designed so that if it does extend beyond the length of the speculum 106 or beyond the viewing lens 104, it does not block the user's vision. For the otoscope 100 illustrated, this is 5.5 cm from one opening to the other.

Figures 17, 18:
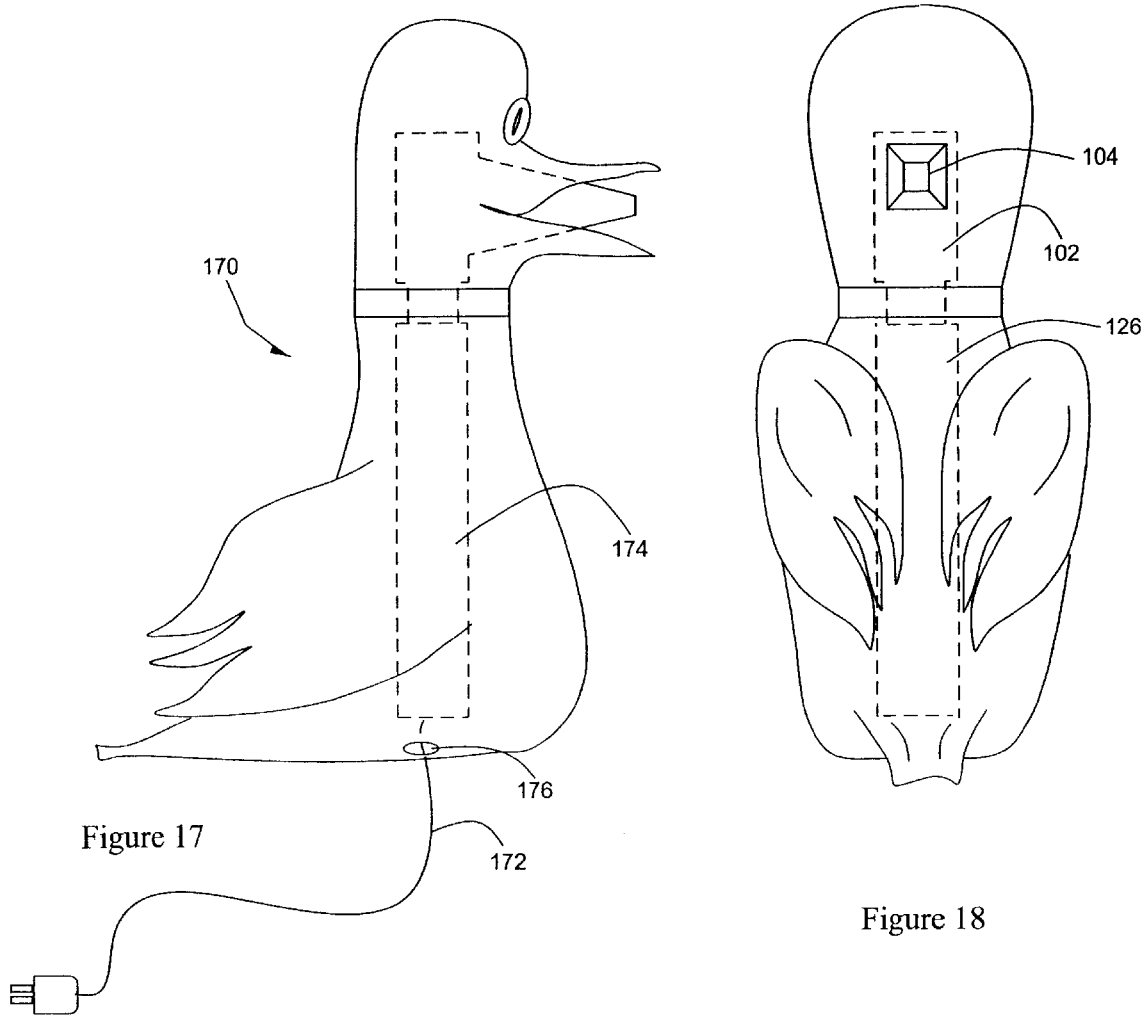
FIG. 17 is a side view of a covered electric otoscope with a hole is manufactured in the bottom of the sleeve to allow for an extension cord to run from the otoscope to a wall socket.
FIG. 18 is a front view of the rear of the covered otoscope illustrating viewing area to allow the examiner to examine the patient.
Figure 19:
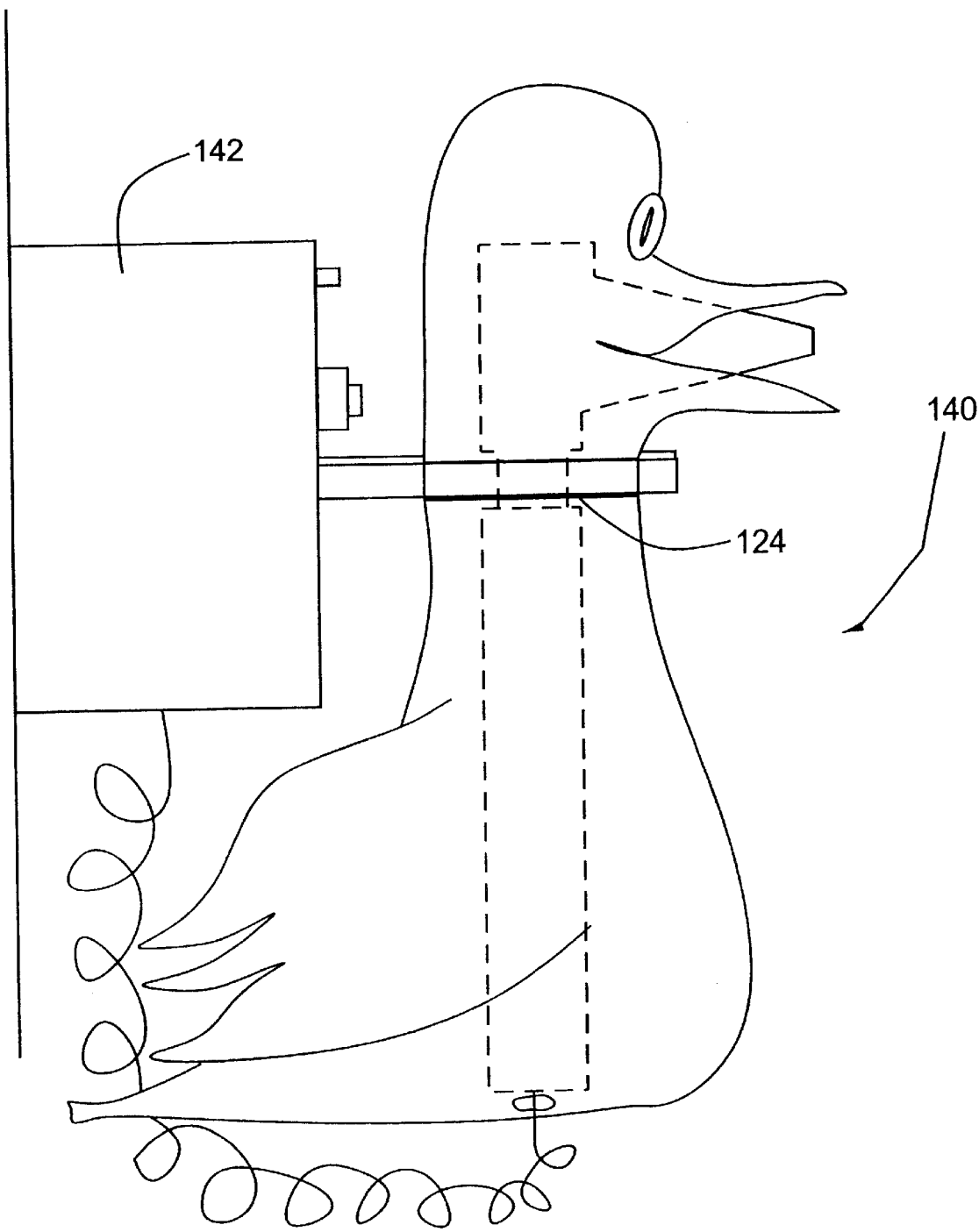
FIG. 19 is a side view of the covered otoscope placed back on a holding rack that is mounted to the wall.

The sleeve 120 is made of a single and/or double layer of material. The double layer of material allows the Pediapet to be stuffed to give form and structure to the animal or object the Pediapet represents. The structure is particularly important for the hood 122 of the Pediapet that covers the head 102 of the instrument so that it does not slip down in front of the optic lens 104 or speculum 106 opening during use. A slit 124 in the sleeve corresponding to the location of the rotating cuff allows for access to the on/off/brightness switch 102. This slit 124 also allows the office otoscopes 140 to be placed back in its holding rack 142 as illustrated in FIG. 19. For those otoscopes 150 that fit into a recharging rack 152, as illustrated in FIGS. 20 and 21, slight alterations are made to the closed end of the sleeve 154. Since contact needs to be made at the base 156 of the handle, either a small hole 158 is made in the closed end of the sleeve 154 to allow for contact, or the closed end is designed so that it can be opened with a strip of Velcro, a snap, a zipper, or other fastening equipment. Similar alterations are made for those Pediapets 170, as illustrated in FIG. 17, that cover otoscopes 174 that are plugged into an electrical cord 172. Since the electrical cord 172 attaches to the base of the handle, a hole or opening 176 is manufactured in the Pediapet 170 sleeve as described above.

For the standard sized otoscope the sleeve is at least 3.0 cm wide to allow for the handle to slide through the sleeve. Areas that need to allow passage of the head through the sleeve are at least 5.0 cm wide.

Some variations in the Pediapet are designed to just cover the handle 126 of the otoscope. These Pediapets correspond to the description of the sleeve above. Others are designed to cover just the head 108 of the otoscope and correspond to the description of the hood above. There are several alternative ways in which the otoscope sleeve and hood can be attached in the event they are not stitched together. These can include snaps, hook and loop material, or other methods that permit the insertion and removal of the otoscope. Alternatively, the hood can be left unattached and simply slid over the otoscope head. This would be applicable when using a cover representing a baseball bat, wherein the handle of the bat would be the handle of the otoscope and easily closed through the use of hook and loop material. A viewing channel would be cut through the bat to coordinate with the viewing lens, as described heretofore. Additional decorative material can be attached to the Pediapet cover to aid in the artistic representation of the object or animal the cover/Pediapet represents. It should also be noted that the dimensions disclosed herein are for example purposes and will vary depending upon the otoscope and Pediapet design.

Ophthalmoscope

The ophthalmoscope 202 is a medical instrument used to examine a patients'eyes. It consists of a handle 232 that may contain a power source and a detachable head 230 which houses an illumination source and optic pieces. The handle 232 of the ophthalmoscope is often times interchangeable with the handle of the otoscope. The handle 232 and head 230 attach at the neck of the ophthalmoscope. Portable ophthalmoscopes are turned off and on by a button and rotating cuff 228 located at the junction of the handle and head of the ophthalmoscope. This cuff 228 also controls the brightness of the light. Some ophthalmoscopes turn on automatically when they are removed from a holding rack that is usually mounted on a wall. These ophthalmoscopes are plugged into a power source and the electrical cord runs from the holding rack to the bottom of the handle of the ophthalmoscope. Still other ophthalmoscopes sit in a charging rack that makes contact with the instrument at the bottom of the handle. These ophthalmoscopes do not have a cord attached to them.

The design of the ophthalmoscope Pediapet is very similar to that of the otoscope Pediapet. There are different sized ophthalmoscopes and slight variations in their shape depending on the company producing the model. This description of the Pediapet is designed to cover the standard sized portable ophthalmoscope. However, scaled down versions, and slight variations are made to the design of the Pediapet to cover other instrument sizes.

The Pediapet is designed to cover the handle 232 and/or the head 230 of the ophthalmoscope 202 while allowing for full function and utility of the instrument. In its ideal form the ophthalmoscope Pediapet 200 consists of a hollow sleeve 210, within the Pediapet 200 body, that is sealed at one end. The sleeve of the Pediapet is approximately 17 cm long, but varies slightly with the design of the animal or object it represents. The Pediapet illustrated in FIGS. 23–29 is made so that the ophthalmoscope slides in handle first through an open end or slit in the sleeve 208 of the Pediapet 200. This covers the handle 202 and in some cases part of the neck of the instrument. A specially designed hood 206 is attached to the sleeve and is pulled up over the head 204 of the ophthalmoscope. The hood is approximately 7.0 cm in length to fit over the head of the instrument. In some cases the hood is an extension of the sleeve 210. Two holes, viewing hole 212 and lens hole 214 are made in the hood 206 to permit the user to examine the patient. In order to ensure unimpaired access through the optic lens, the viewing hole 212 must measure at least about 1.0×1.0 cm. The lens hole 214, directly opposite; is at least 1.0×1.5 cm in diameter. These holes are connected and aligned to permit an unobstructed view of the patient's eye.

The sleeve 210 is made of single and/or double layers of material, with the double layer of material allows the Pediapet to be stuffed. This helps give form and structure to the animal or object the Pediapet represents. The structure is particularly important in preventing the hood 206 of the Pediapet 200 covering the head 204, from slipping down in front of the optic lens during use. The slit 208 in the sleeve 210 preferable serves to permit access to the on/off/brightness switch as well as enable easy insertion of the ophthalmoscope 200. This slit 208 also allows the office ophthalmoscopes 250 of FIG. 18, to be placed back in its holding rack 252. Additional slit(s) 220, are made in the side of the hood 206 to allow access to a focusing knob 220, and in the front of the hood 212 to access an aperture wheel and the switch to change light color. Variations in the design of the head cover must maintain the focusing knob, aperture and light switch sufficiently exposed to enable use.

Figures 27, 28:
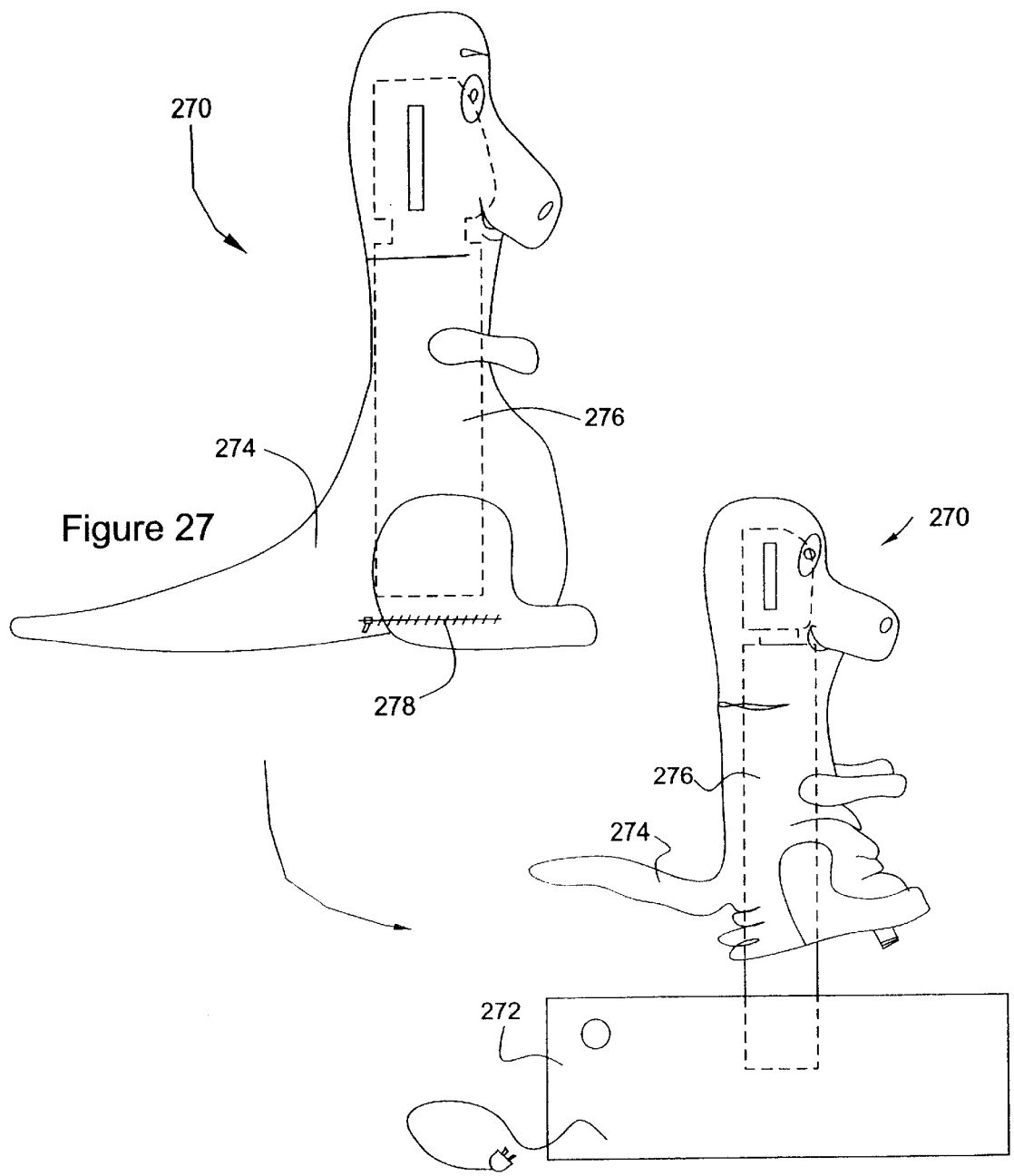
FIG. 27 is a side view of an ophthalmoscopes cover to accommodate rechargeable batteries.
FIG. 28 is a side view of the rechargeable ophthalmoscope of FIG. 27 placed into the recharger.

For those ophthalmoscopes 270, as illustrated in FIGS. 27 and 28, that fit into a recharging rack 272, slight alterations are made to the closed end of the sleeve 274. Since contact needs to be made at the base of the handle 276, either a small hole 278 is made in the closed end of the sleeve 274 to allow for contact, or the closed end is designed so that it can be opened with a strip of Velcro, a snap, a zipper, or other fastening equipment. Similar alterations are made for those Pediapets 290 that cover ophthalmoscopes using an electrical cord 292, as illustrated in FIG. 25. Since the electrical cord 292 attaches to the base of the handle, a hole 294 or opening is manufactured in the Pediapet sleeve as described above.

For the standard sized ophthalmoscope the sleeve is at least about 3.0 cm wide to allow for the handle to slide through the sleeve. Areas that need to allow passage of the head through the sleeve are at least about 4.0 cm wide. These dimensions will vary dependent upon the make of the ophthalmoscope and design of the pet.

Some variations in the Pediapet are designed to only cover either the handle or head of the ophthalmoscope. These Pediapets correspond to the description of the sleeve or hood above. As with the Pediapet for the otoscope, there are several alternative ways in which the ophthalmoscope can be inserted into the sleeve of the ophthalmoscope Pediapet and are described heretofore. As with the otoscope, additional decorative material can be attached to aid in the artistic representation of the object or animal.

Blood Pressure Cuff

Figure 30:
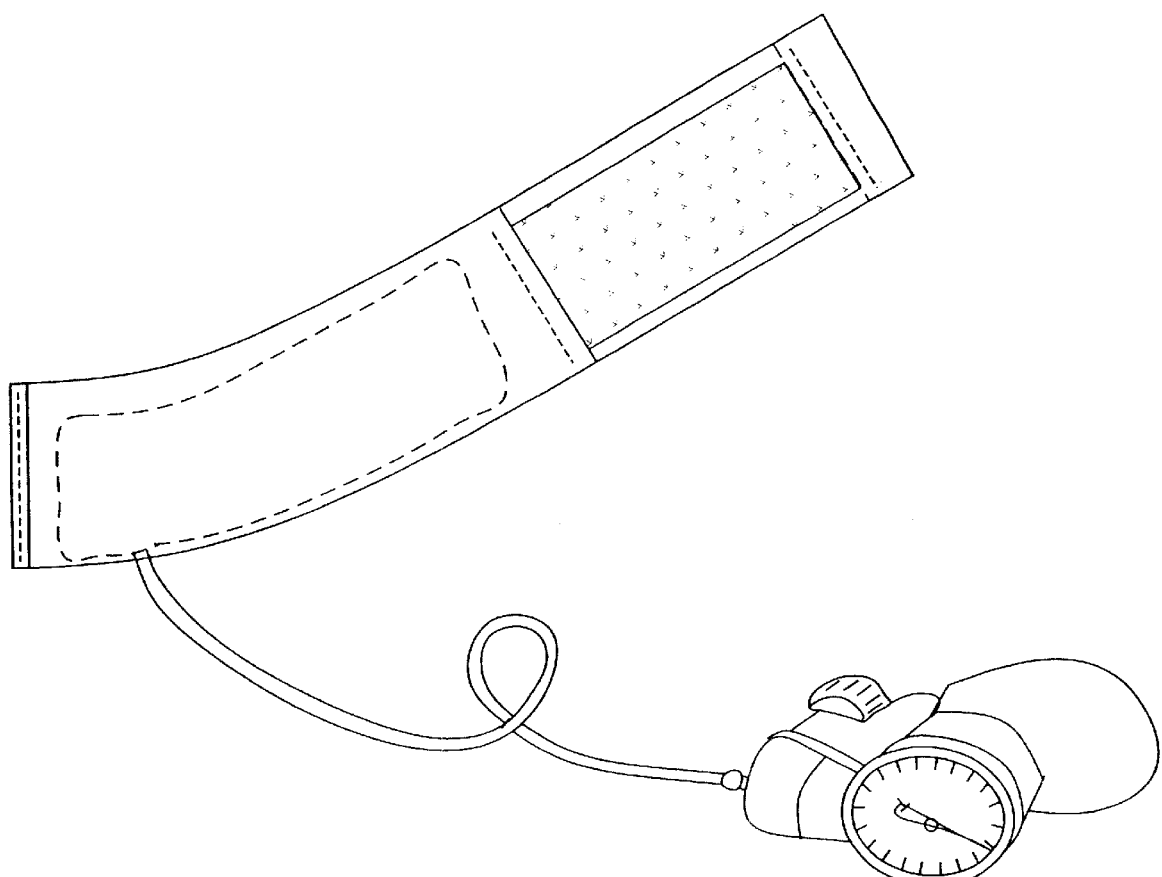
FIG. 30 is a perspective view of a standard blood pressure cuff.

The blood pressure cuff, as illustrated in FIG. 30, is used to measure a patient's systolic and diastolic blood pressure. It consists of a cuff that fastens around a patient's limb, a rubber bladder that is inflated to expand the cuff, a rubber tube of variable length that connects the bladder to an inflation bulb, and a gauge. The gauge can be mounted to the cuff, to the inflation bulb, or on the wall. Still other gauges hang freely from the cuff by means of a second rubber tube.

Figure 31:
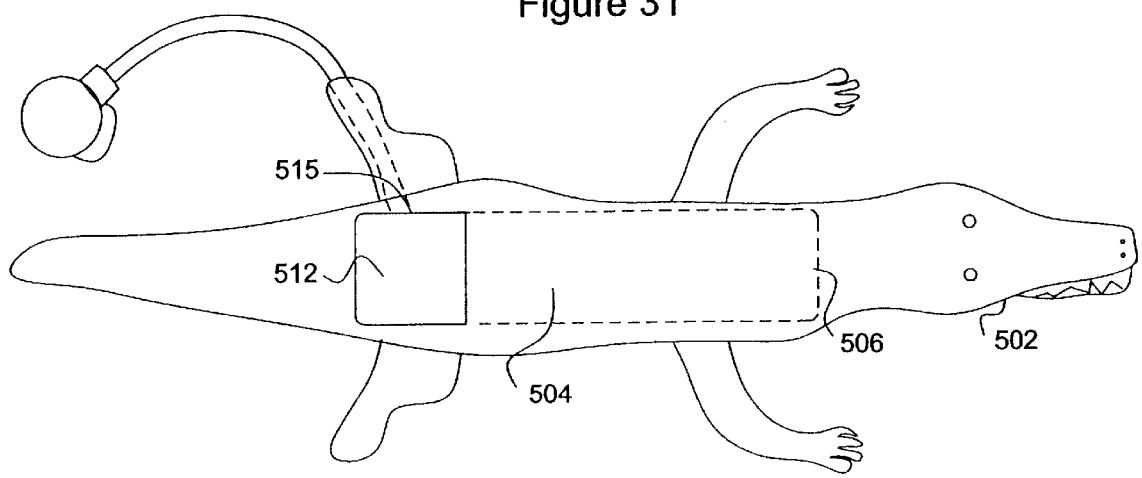
FIG. 31 is a top view of an alligator cover for the blood pressure cuff of FIG. 30.
Figure 32:
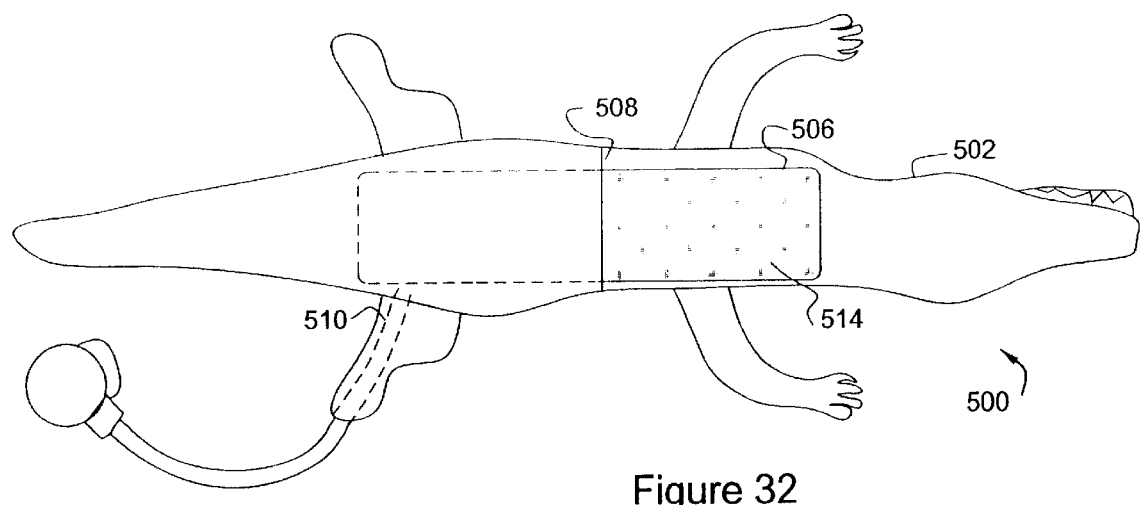
FIG. 32 is a bottom view of the alligator cover of FIG. 31.

In its ideal form, the blood pressure cuff Pediapet as illustrated in FIGS. 31 and 32, will consist of a sleeve 502 that looks like an animal and/or other familiar object, such as an alligator 500. The blood pressure Pediapet cover functions as a sleeve 502 to encircle a patient's arm or leg, and is designed to contain the inflatable bladder 504 of the blood pressure cuff 506. The dimensions of the sleeve 502 are approximately that of standard adult or pediatric blood pressure cuffs 506, 14×55 cm and 11×35 cm respectively. The sleeve 502 is constructed from a double layer of fabric or other flexible material. On the side of the Pediapet contacting the patient, is a pocket 508 into which the inflatable bladder 504 is inserted. Starting at one inside edge of the sleeve 502, the pocket 508 is approximately one third to one half of the total sleeve area. The pocket measures about 29 cm long and 14 cm wide for the adult size, and 20 cm long and 10.5 cm wide for the pediatric size. To allow the rubber tube, or tubes, to connect to the bladder, a hole 510 is made in the long edge of the pocket. This hole 510 is approximately 1–2 cm in length and is located approximately 4–7 cm in from the short, outside edge of the pocket. In the optimum embodiment, the tube is run through one of the Pediapet's legs.

Hook and loop material is used to secure the Pediapet around the patient's limb. The hook portion 512 is located on the outside of the Pediapet, and measures approximately 11×10.5 cm for the adult Pediapet, and 5×8 cm for the pediatric Pediapet. On the inside of the Pediapet, a large section of loop material 514 is attached to the end opposite the end of the loop material 512. This section of loop material 514 measures about 25.5×10.5 cm for the adult size and 15×6.5 for the child size. It should be noted that the foregoing dimensions are approximate and are provided herein as examples and ratios only and not intended to limit the scope of the invention.

The outside of the blood pressure Pediapet can have an extra piece or pieces of fabric cut and sewn into the shape of the object and/or animal that the Pediapet is designed to portray. Stuffing can be contained between the layers of fabric to aid in giving the Pediapet the appearance of the animal and/or objects.

The hook material 512 either is left exposed, or is minimally covered by a flat piece of fabric. If one part of the Pediapet overlays the hook material 512, it is designed so that it may be lifted out of the way, folded back and secured, or removed when the Pediapet is being used to measure blood pressure. A stuffed head, legs, tail, tree branches or other objects may extend beyond the minimum measurements of the sleeve in order to aid in the portrayal of the object. The flexible rubber tube or tubes may fit through one of these extensions forming a small sleeve through which the tube may be threaded.

In an alternative design, the Pediapet is manufactured as a cover to fit over a preexisting blood pressure cuff. In this design, the existing cuff slides into a sleeve that is designed to look like part of an object and/or animal. The Pediapet cover is then secured around the cuff by means of a zipper, Velcro, snaps, tie strings, or other fastening equipment. The part of the sleeve coming in contact with the patient, in general, consists of one layer of fabric and does not have any stuffing in between it and the cuff. The outside part of the sleeve consists of one to several layers of fabric and contains variable amounts of stuffing to aid in the representation of the object and/or animal the sleeve portrays. Additional decorative material may be attached to the outside of the sleeve to also aid in portrayal. A hole is made in the bottom edge of the cover corresponding to the entrance of the flexible rubber tube into the bladder of the cuff. As with the first design, a stuffed head, legs, tail, tree branches or other objects may extend beyond the minimum measurements of the cover in order to aid in the portrayal of the object. Often, these parts of the Pediapet contain stuffing. The flexible rubber tube or tubes may fit through one of these extensions forming a small sleeve through which the tube may be threaded.

IV Pole

Figure 33:
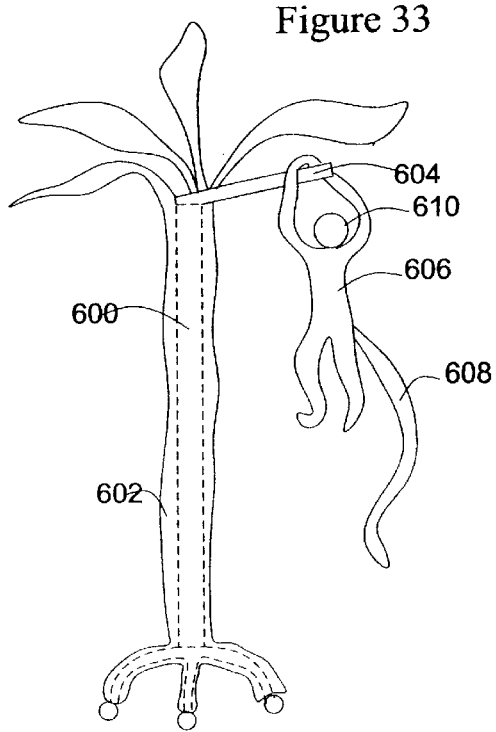
FIG. 33 is a front view of an IV pole covered to look like a palm tree.

IV poles can be quite intimidating for children and adults as they are generally used in hospital settings and require the use of a needle. To "soften" the appearance, the IV pole 600, illustrated in FIG. 33, is covered with a coconut tree trunk 602 with fonts at the top of the trunk 602. The support pole 604 in this Figure is not covered, however, this is dependent upon the Pediapet design. A monkey 610 containing the bag of IV fluid 606 is hanging off the support pole 604. The monkey 610, or other figure, must be dimensioned to permit the standard IV bag, or other medical apparatuses, to be hung in the standard fashion so as to permit the apparatus to function. If the bag 606 is merely placed into the stomach of a stuffed animal, it would drop and hamper the fluid flow. The bag 606 can be either connected to the monkey's head or an access hole can be provided in the back of the monkey to accept the standard hanging element associated with the IV. The preferred method will become apparent to those skilled in the art and will be dependent upon the apparatus and Pediapet design. In this Figure, the tail 608 of the monkey 610 is used as the IV tube. This can be covered, however for medical safety it may be desirable to leave the tail uncovered. The tree trunk 602 is manufactured from two pieces of material with stuffing in between to simulate the tree trunk. The tree fonts can be manufactured from green felt or other appropriate material. The trunk 602 can be secured, once wrapped around the IV pole 600, through use of hooks, snaps, hook and loop material, etc. The dimensioning of the trunk 600 must be such that it does not interfere with the standard functionality of the IV pole, i.e., the wheels must be free to move, it must continue to pass through doors, be lightweight, etc.

The IV pole can easily be covered to resemble any elongated item, such as a space ship, building or monument. For example, the IV pole could be the Empire State Building and the IV bag King Kong.

Crutches

Figure 34:
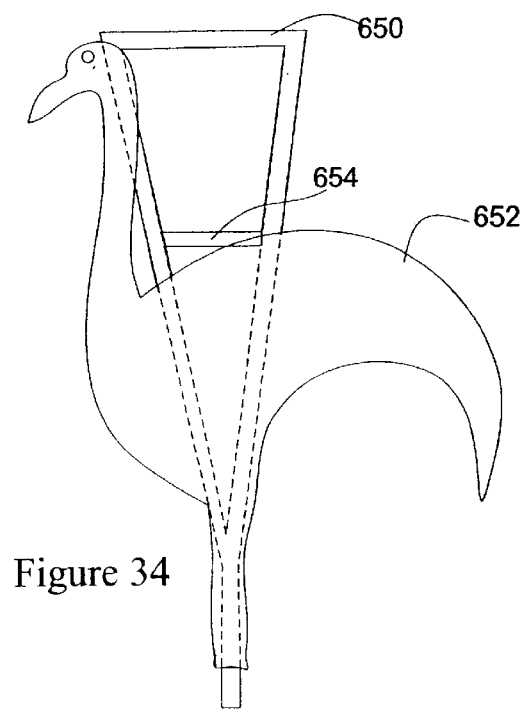
FIG. 34 is a front view of a crutch covered to look like a flamingo.

Although crutches are not as intimidating as the majority of medical instruments, they still reflect an inability of the patient to function in their usual manner. To make using crutches more fun, Pediapets can be affixed to the crutch. In FIG. 34 a crutch has been covered with a flamingo 652. The flamingo 652 is a stuffed figure that is attached to the crutch 650 through use of tabs, etc., as disclosed heretofore in relation to the stethoscope. Preferable the back of the flamingo 652 is below the hand grip 654 to avoid interfering with the patient's use. This, however, is dependent upon the design and some designs, such as a knurled tree, can incorporate the hand grip 654 into the design.

Wheelchair

Figure 35:
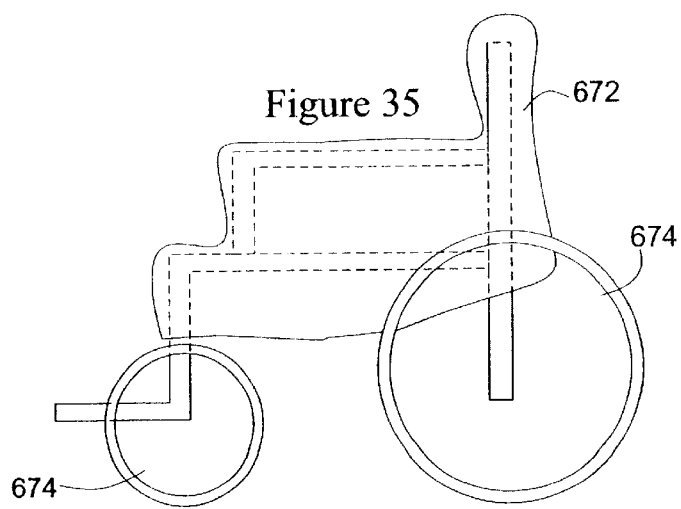
FIG. 35 is a side view of a wheel chair covered to look like a throne.

In FIG. 35 the wheelchair 670 is covered to appear as a throne by placing a throne cover 672 over the chair 670. The throne cover 672 must be dimensioned to securely fit over the chair 670 without interfering with the wheels 674. The cover 672 should be stuffed to portray a throne while accommodating all parts of the wheelchair 670. A strap can, if necessary, be provided to run under the seat of the wheelchair 670 to maintain the preferred snugness as well as keep the cover away from the wheels 674. The throne cover can also be an animal, such as a bear, or an object, such as a rocket seat, that is stuffed to provide the appropriate appearance.

The materials used for the foregoing Pediapets must be appropriate to the end use, i.e. elephant trunks must be flexible, as should the "tree" branches. All materials are preferably easy to clean and allergy free. The material must also have the ability to hold up under repeated washings. At least some level of water repellency is additionally beneficial. Preferably the materials chosen are soft, providing the comfort associated with stuffed animals, although, again, this would be dependent upon the animal or object portrayed. The material chosen for manufacture will determine the method of construction, i.e. fabric is sewn or melt-glued or other methods applicable to the chosen fabric, plastics can be molded or extruded.

Additional Embodiments

Figure 36:
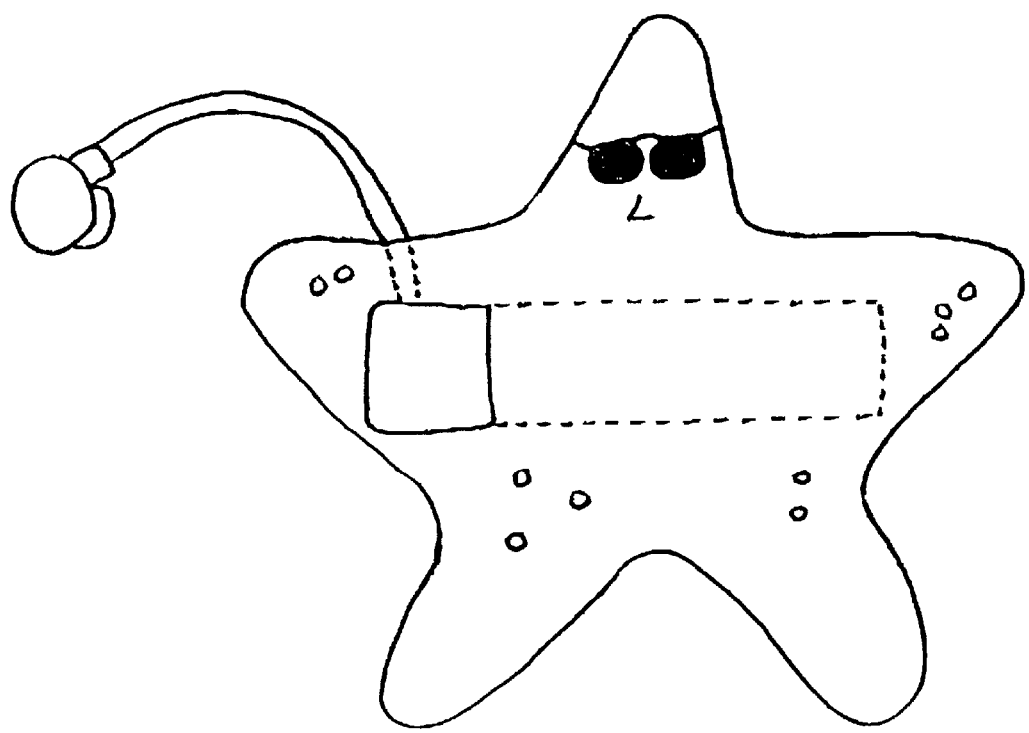
FIG. 36 is a top view of a blood pressure cuff covered by a depiction of a starfish.

FIG. 36 shows another embodiment in which a starfish is used in place of the alligator of FIG. 31. The starfish embodiment of FIG. 37 corresponds to the illustration of FIG. 32. Other embodiments can include other relatively flat bodied animals in addition to alligators and starfish. Fish are particularly suitable for encapsulating the blood pressure cuff. Among the fish that can be used are any of various stingrays of the family Dasyatidae, having a whiplike tail. It is also called stingaree. Additionally the animal can be a Manta. Manta is any of several rays of the family Mobulidae, inhabiting tropical and subtropical seas and having a large flattened body, winglike pectoral fins, a whiplike tail, and two hornlike fins that project forward from the head. In this sense, also called devilfish, manta ray, sea devil.

Figure 38:
FIG. 38 is a top view of a blood pressure cuff covered by a depiction of a bear-like animal.
Figure 39:
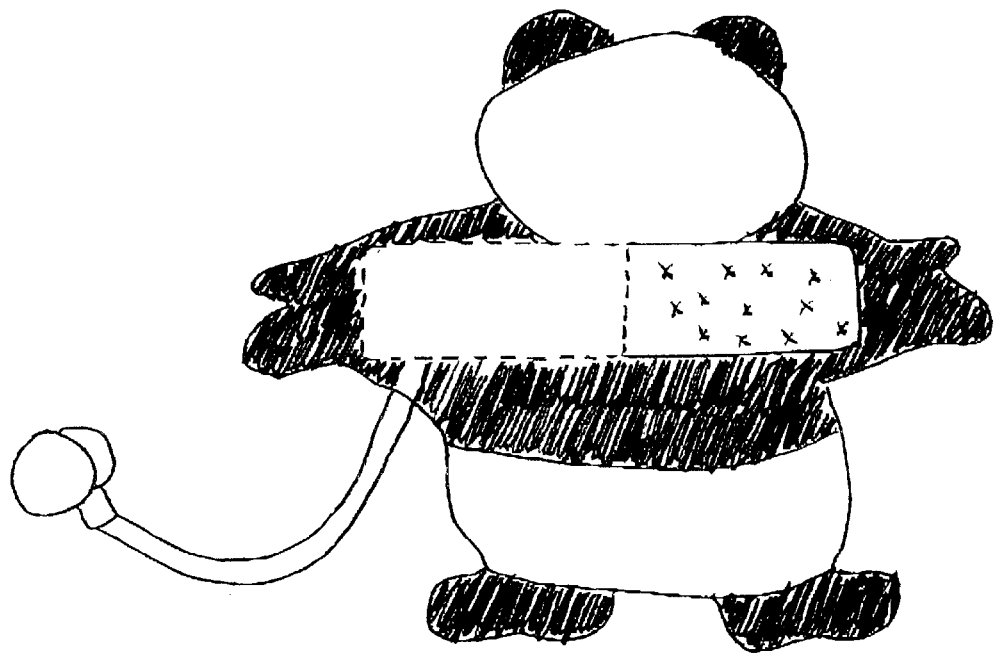
FIG. 39 is a bottom view of the embodiment of FIG. 38.

FIGS. 38 and 39 illustrate a bear like animal, in particular a teddy bear or panda. The bear or bear like animal is preferably used in an essentially flat version with the cuff extending from one paw to the other.

Other animals include the ferret, a weasel like, usually albino mammal. Other weasel like animals include the mink, any of various semiaquatic carnivores of the genus Mustela, especially *M. vison* of North America, resembling the weasel and having short ears, a pointed snout, short legs, and partly webbed toes.

Figure 40:
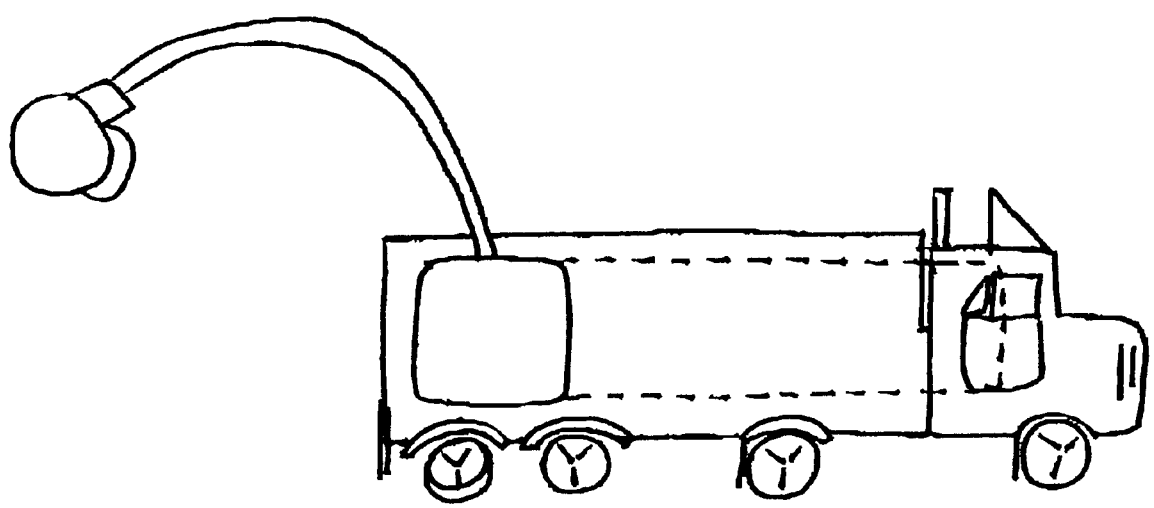
FIG. 40 is a top view of a blood pressure cuff covered by a depiction of a truck-like vehicle.

FIG. 40 shows a different variation in which the blood pressure cuff is enclosed within a decorative replica of a truck. As in the case of the bear, the cover is formed from two layers of fabric and is essentially a flat cover.

Figure 41:
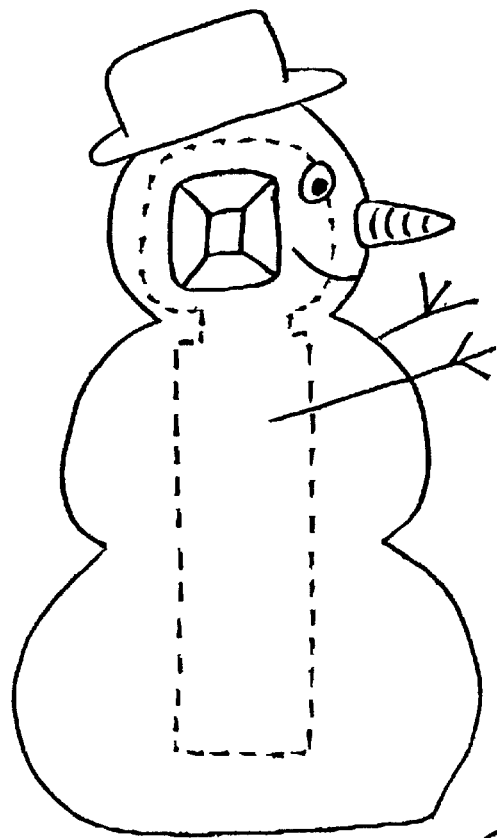
FIG. 41 is a side view of a covered ophthalmoscope showing a shroud that is a depiction of a snowman like structure.
Figure 42:
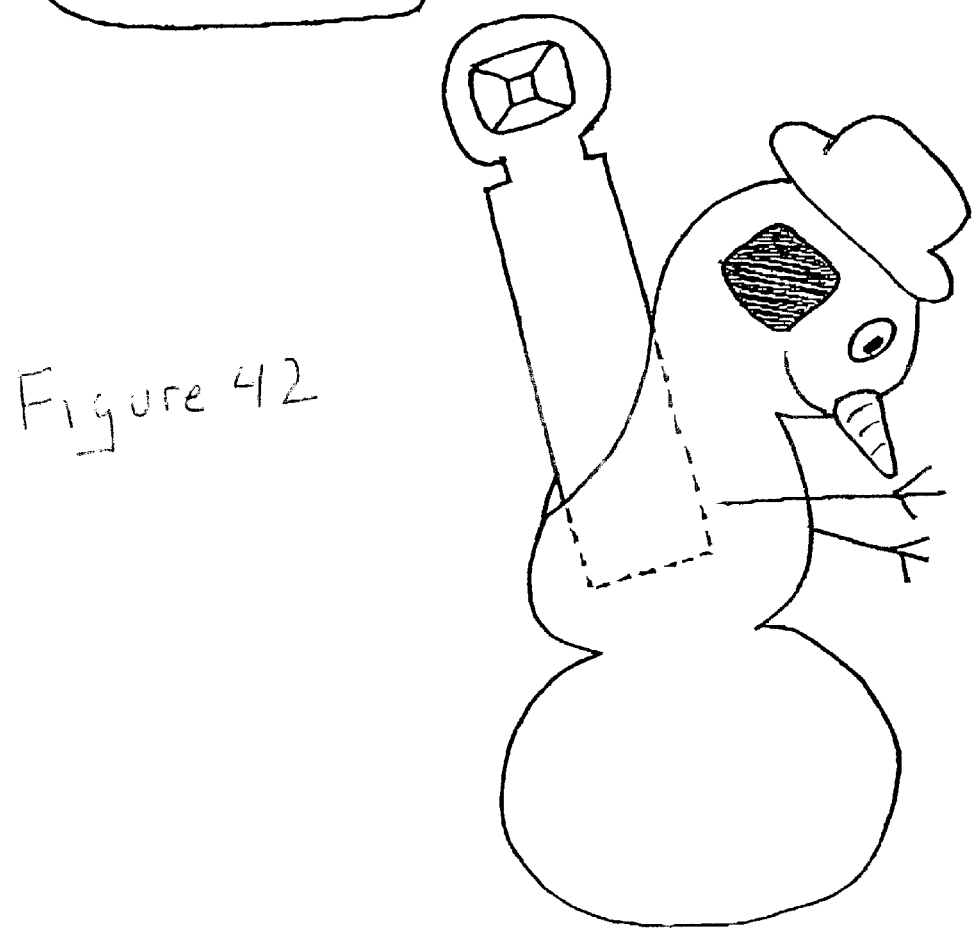
FIG. 42 is a side view of an ophthalmoscope being placed into the cover of FIG. 41.

FIGS. 41 and 42 illustrate a snow man cover for an ophthalmoscope. FIG. 42 shows the ophthalmoscope being inserted into the snow man cover. Similarly, FIGS. 43 and 44 illustrate a rabbit cover employed in a manner similar to the embodiments of FIGS. 41 and 42, as well as the embodiments of FIGS. 23 through 29.

Figure 45:
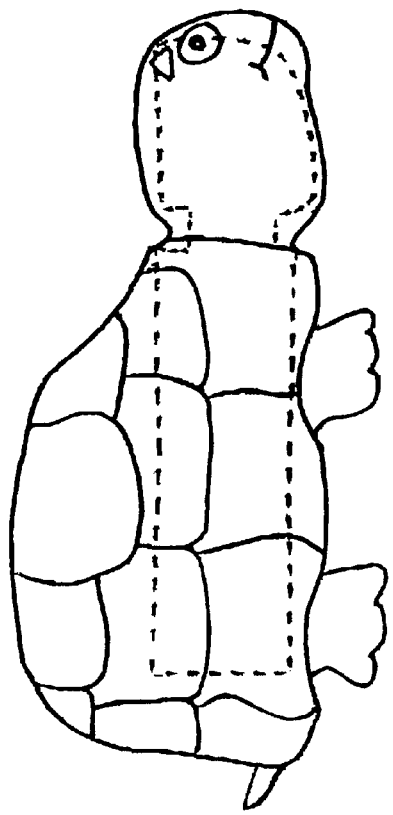
FIG. 45 is a side view of a covered ophthalmoscope showing a shroud that is a depiction of a turtle-like structure.
Figure 46:
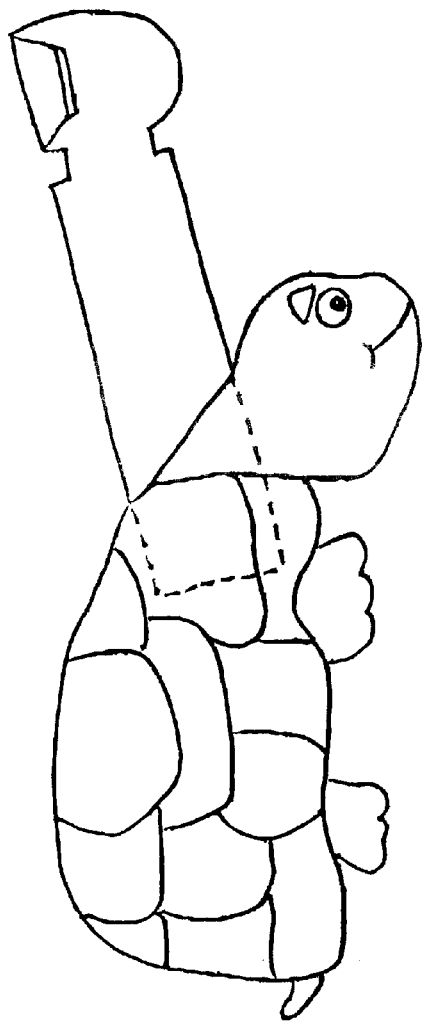
FIG. 46 is a side view of an ophthalmoscope being placed into the cover of FIG. 45.
Figure 47:
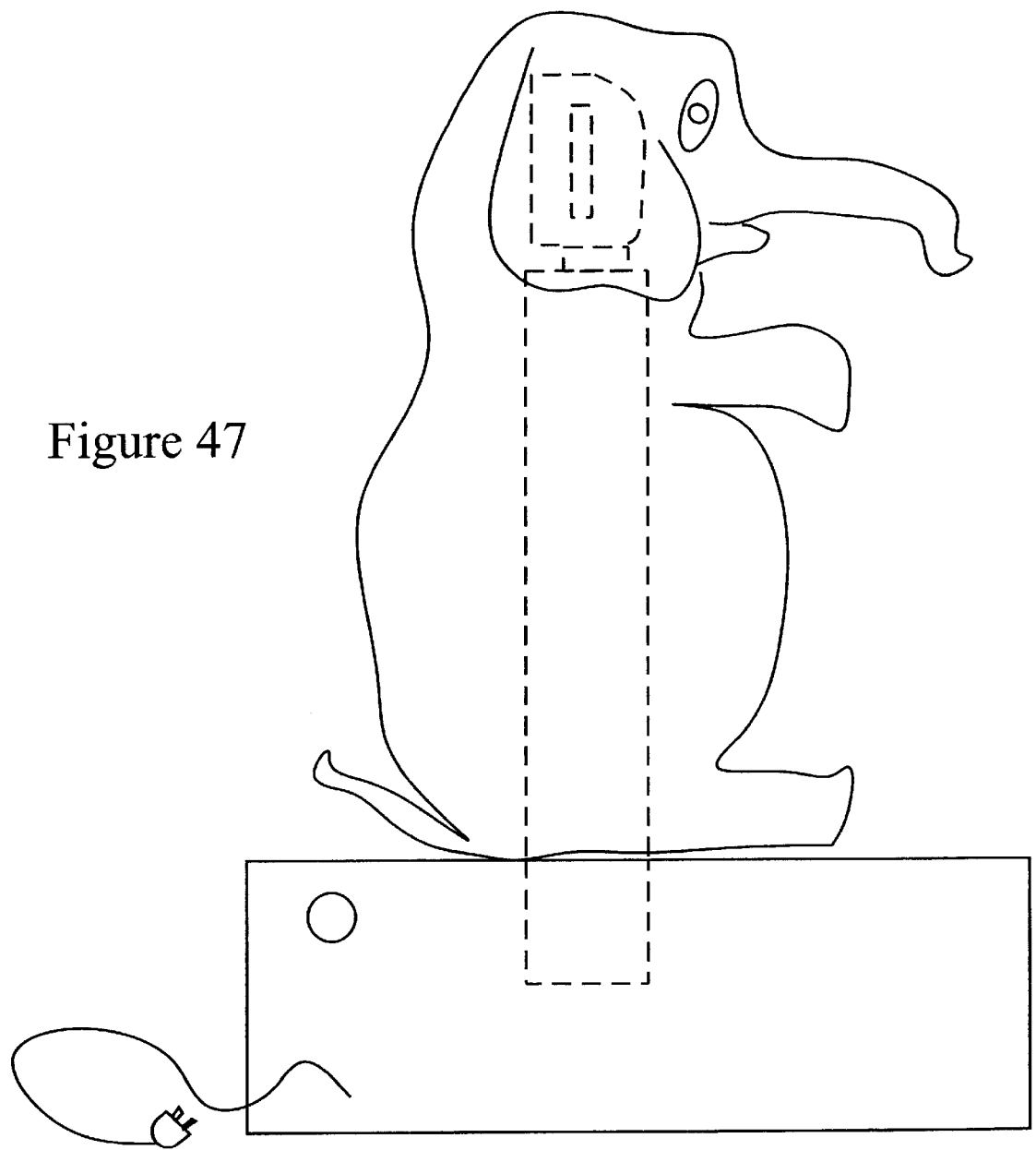
FIG. 47 is a side view of a covered ophthalmoscope showing a shroud that is a depiction of a elephant-like structure.

FIGS. 45 and 46 illustrate turtle embodiments while FIG. 47 illustrates an elephant embodiment. It should be noted that the illustration of FIG. 47 corresponds to the embodiment of FIG. 28.

Figure 50:
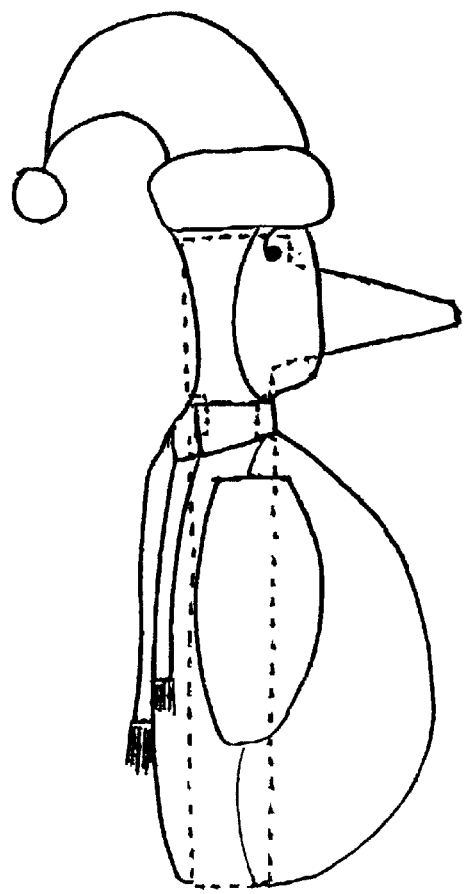
FIG. 50 is a side view of a covered otoscope showing a shroud that is a depiction of a penguin-like structure.
Figure 51:
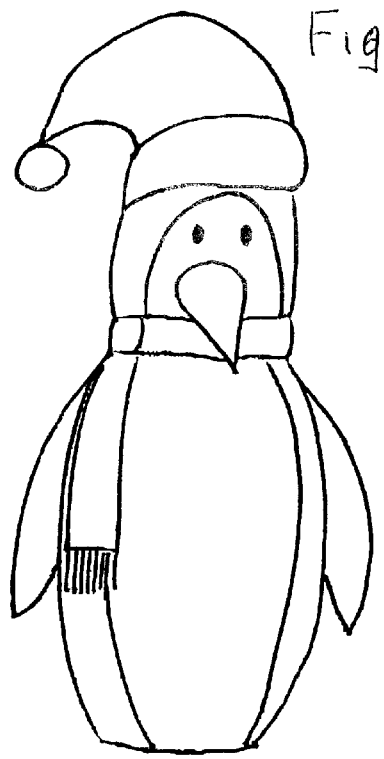
FIG. 51 is a front view of a shroud that is a depiction of a penguin-like structure.
Figure 52:
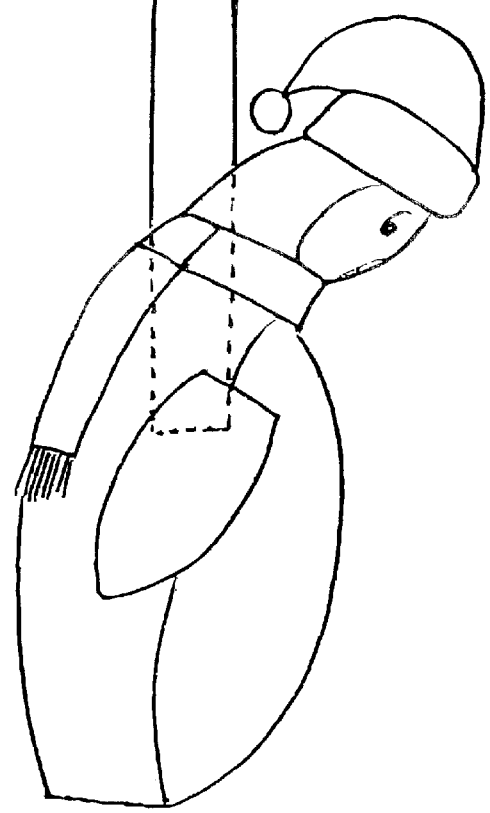
FIG. 52 is a side view of an otoscope being placed into the cover of FIG. 50.

FIGS. 48 and 49 illustrate otoscope covers in the form of a train. Similarly, the cover can be in the form of a truck FIGS. 50, 51 and 52 illustrate a penguin type of otoscope cover.

It should be noted that the type of objects previously illustrated as covers for the otoscope can also be used for the ophthalmoscope and those illustrated for the ophthalmoscope can also be used for the otoscope.

In the case of the elephant, the truck can be used to enclose the speculum. With bird like animals, the beak can be used to enclose the speculum.

The goal of the Pediapet is to increase the comfort level of a patient during an examination and/or use of medical equipment. It is therefore important that the appearance of the product addresses this point. Although a number of materials can be used to make the foregoing, all materials should be appropriately chosen for the end use. It should also be noted that the illustrated Pediapets, as well as their dimensioning, are used as examples only. Further, the medical equipment disclosed herein are for examples only and are not intended to limit the scope of the invention. Those skilled in the art will be aware of alternate designs and appropriate dimensioning that will corresponding with the selected medical equipment.

What is claimed is:

1. The method of examining a patient, using a medical examination instrument for the examination of a body part, said instrument having a distal end and a proximal end and comprising a light source and a optical viewing element, said optical viewing element being at said instrument proximal end, comprising the step of inserting said medical instrument into said three dimensional representation of an object unrelated to a medical instrument, said object having an upper region, and said upper region having at least one opening, positioned said optical viewing element within said upper region, aligning said optical viewing element with an opening in upper region, and said viewing said body part through at least one opening in said upper region.

2. The method of claim 1, wherein said object is a three dimensional representation of an animal, said animal having a head region and said head region having an eye region and a region resembling an animal's mouth, positioning said animal head region being proximate said instrument distal end, aligning said optical viewing element with an opening in animal head region, and viewing said patient body part through at least one opening in said head region.

3. A medical examination instrument for the examination of a body part, said instrument having a distal end and a proximal end and a three dimensional representation of an animal, said medical instrument being substantially within said three dimensional representation of a non-medical object.

4. The medical examination instrument of claim 3, said instrument further comprising a light source and a optical viewing element, said optical viewing element being at said instrument proximal end, said non-medical object being animal having a head region, said head region having an eye region and a region resembling an animal's mouth, said animal head region being proximate said instrument distal end, said optical viewing element being positioned within said head region such that a user can see through at least one opening in said head region.

5. The medical instrument of claim 4, wherein said optical viewing element is aligned with said eye region, whereby an optical light path is provided through said representation of an animal and though said medical instrument, said optical path being through said animal's mouth.

6. The medical instrument of claim 4, wherein said optical viewing element is aligned with said eye region, whereby an optical light path is provided through said representation of an animal and though said medical instrument, said optical path being through said animal's eye region.

7. The medical instrument of claim 4, wherein said optical viewing element is aligned with said eye region, whereby an optical light path is provided through said representation of an animal and though said medical instrument, wherein said optical viewing element is a magnifying lens.

8. The medical instrument of claim 4, wherein said optical viewing element is aligned with said eye region, whereby an optical light path is provided through said representation of an animal and though said medical instrument, wherein said instrument is an otoscope.

* * * * *

UNITED STATES PATENT AND TRADEMARK OFFICE
CERTIFICATE OF CORRECTION

PATENT NO. : 6,520,639 B2
DATED : February 18, 2003
INVENTOR(S) : David B. Avner It is certified that error appears in the above-identified patent and that said Letters Patent is hereby corrected as shown below:

Columns 1-16, should be deleted to appear as per attached columns 1-16.

Signed and Sealed this

Twenty-sixth Day of October, 2004

JON W. DUDAS
*Director of the United States Patent and Trademark Office*

DECORATIVE COVERS FOR MEDICAL EQUIPMENT

CROSS-REFERENCE TO RELATED APPLICATION

This application is a continuation-in-part of copending patent application Ser. No. 09/200,134 filed Nov. 25, 1998, and claims the benefit of Provisional appl. No. 60/066812, filed Nov. 26, 1997, the disclosure of which is incorporated herein by reference, as though recited in full.

FIELD OF THE INVENTION

This invention relates to the production of a decorative covering, also referred to from here on out as a Pediapet, that will be used to cover or partly cover medical equipment in such a way that the equipment will appear less threatening to patients. In particular, this invention relates to the production of decorative covers in the shape of animals and other familiar objects that will be used to cover medical equipment such as stethoscopes, ophthalmoscopes, IV poles, crutches, blood pressure cuffs, syringes etc. and will help make the instrument or part of the instrument appear as though it is part of that animal or object.

BACKGROUND OF THE INVENTION

Visits to the hospital or doctor's office can be a scary and anxiety provoking experience for many patients, particularly in a pediatric setting. The fear and anxiety of being in a new surrounding, confronted by new faces and foreign instruments can stimulate a sympathetic nervous response in patients leading to such objective physical findings as increased heart rate, increased blood pressure, sweating, emotional liability, and changes in arterial blood gases. Most doctors find that it is advantageous to try to relieve these fears and anxieties before and throughout a physical exam or procedure. This allows the patient to feel more at ease during the exam which in turn gives the health care provider more accurate information about the patients health.

This had been recognized as a problem as problem and has been addressed in the prior art, such as U.S. Pat. No. 5,592,946 where they note that young patients are intimidated by the stethoscope. The '946 patent, however, primarily addresses the allergic reaction some health professionals have to the latex stethoscope tubing.

The disclosed medical instrument covers goes beyond any prior art covers by covering the instrument with a cover that makes it look like a familiar object, such as a stuffed animal. These covers are an easy way to distract and relax a young patient during a medical examination and/or procedure, making the instrument less threatening. Additionally, the covered instrument may be used to playfully distract a child during the exam and/or procedure.

SUMMARY OF THE INVENTION

The Pediapets are decorative covers in the shape of familiar objects such as animals, trees, clothing, etc. that are used to cover medical equipment that in turn is used during physical examinations and medical procedures. The covers are attached to the instrument in such a way as to give the medical instrument or part of the instrument the appearance of the object that the cover represents.

BRIEF DESCRIPTION OF DRAWINGS

Figure 9:
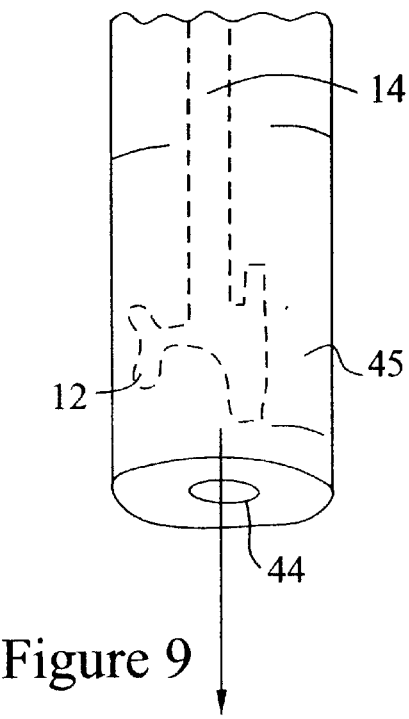
FIG. 9 is a perspective view of one embodiment of covering the bell/diaphragm with the cover extending beyond the bell/diaphragm.
Figures 15, 16:
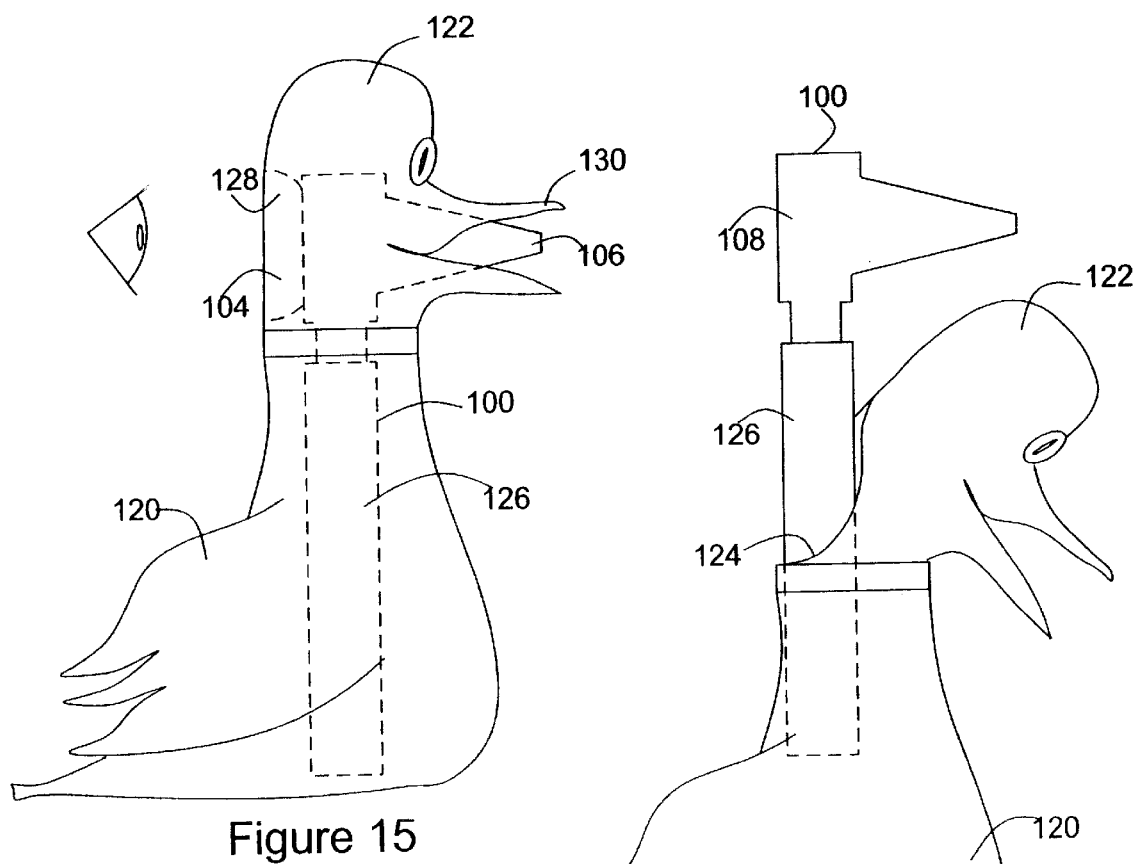
FIG. 15 is a side view of a duck cover placed over an otoscope.
FIG. 16 is a side view of the otoscope being inserted into the cover.
Figure 22:
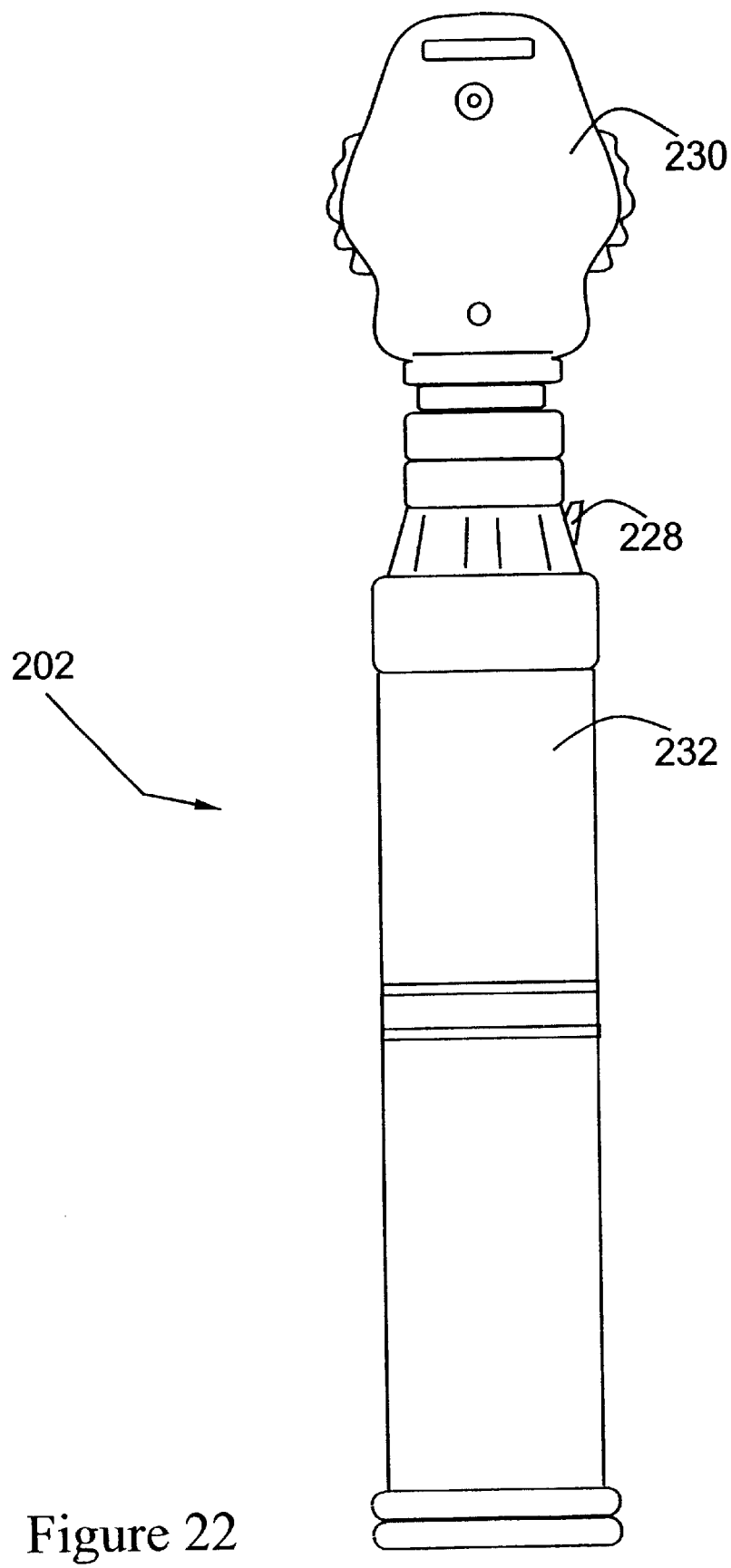
FIG. 22 is a front view of the rear of an ophthalmoscope.
Figure 29:
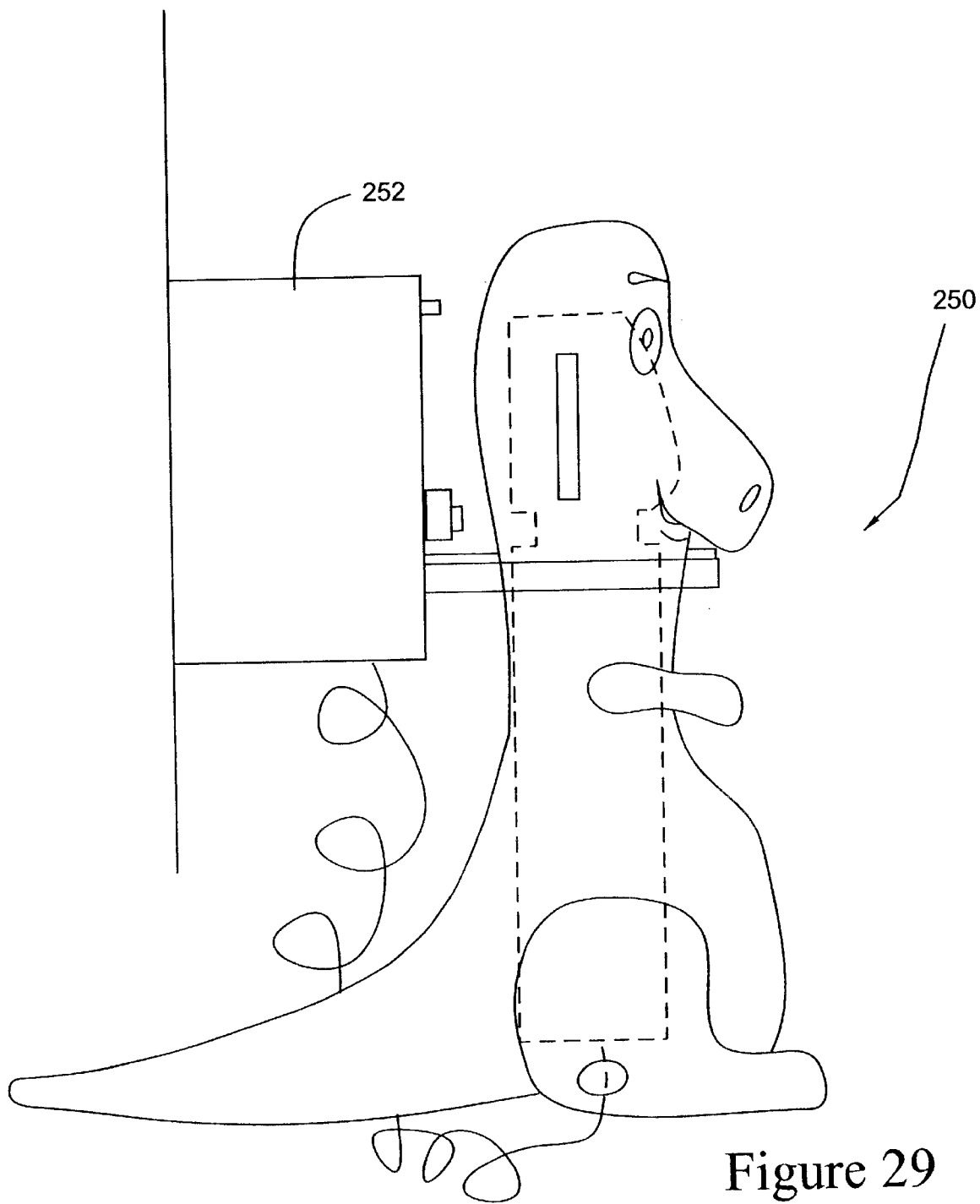
FIG. 29 is a side view of the covered ophthalmoscope placed into a holding rack.
Figure 37:
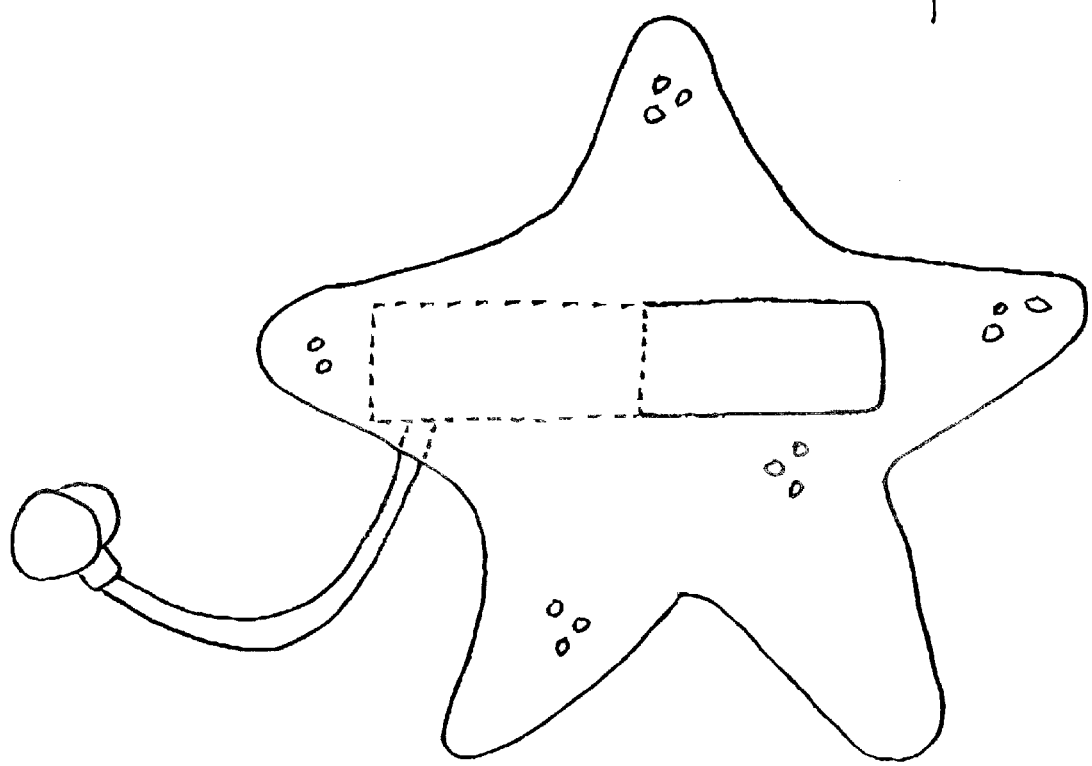
FIG. 37 is a bottom view of the embodiment of FIG. 36.

FIG. 1 is a perspective view of a standard stethoscope;

FIG. 2 is a front view of a stethoscope cover taking the form of an elephant;

FIG. 3 is a front view of a stethoscope cover in the form of a giraffe;

FIG. 4 is a front view of a stethoscope having an animal placed on the Y shaped tubes;

FIG. 5 is a front view of a man's tie covering for use with a stethoscope;

FIG. 6 is a front view of the back of the elephant illustrating the attachment method;

FIG. 7 is a front view of the back of the of the elephant illustrating an alternate attachment method;

FIG. 8 is a front view of the back of the of the elephant illustrating an additional attachment method;

FIG. 9 is a perspective view of one embodiment of covering the bell/diaphragm with the cover extending beyond the bell/diaphragm;

FIG. 10 is a perspective view of another embodiment of covering the bell/diaphragm end of the cover with the bell/diaphragm extending beyond the cover;

FIG. 11 is a perspective view of an additional embodiment of covering the bell/diaphragm with a slit being provided for the bell/diaphragm;

FIG. 12 is a perspective view of an alternative embodiment of covering the bell/diaphragm wherein the end of the cover is attached to the bell/diaphragm;

FIG. 13 is a side view of an assembled otoscope;

FIG. 14 is a front view of the detached head of the otoscope;

FIG. 15 is a side view of a duck cover placed over an otoscope;

FIG. 16 is a side view of the otoscope being inserted into the cover;

FIG. 17 is a side view of a covered electric otoscope with a hole is manufactured in the bottom of the sleeve to allow for an extension cord to run from the otoscope to a wall socket;

FIG. 18 is a front view of the rear of the covered otoscope illustrating viewing area to allow the examiner to examine the patient;

FIG. 19 is a side view of the covered otoscope placed back on a holding rack that is mounted to the wall;

FIG. 20 is a side view of a cover designed to accommodate an otoscopes that fits into a recharging rack;

FIG. 21 is a side view of the otoscope of FIG. 20 placed into the recharging rack;

FIG. 22 is a front view of the rear of an ophthalmoscope;

FIG. 23 is a side view of a covered ophthalmoscope;

FIG. 24 is a side view of the ophthalmoscope being placed into the cover;

FIG. 25 is a side view of an additional cover for an electric ophthalmoscope including a hole to accommodate a cord;

FIG. 26 is a front view of the back of the ophthalmoscope illustrating the hole to accommodate the lens;

FIG. 27 is a side view of an ophthalmoscopes cover to accommodate rechargeable batteries;

FIG. 28 is a side view of the rechargeable ophthalmoscope of FIG. 27 placed into the recharger;

FIG. 29 is a side view of the covered ophthalmoscope placed into a holding rack;

FIG. 30 is a perspective view of a standard blood pressure cuff;

FIG. 31 is a top view of an alligator cover for the blood pressure cuff of FIG. 30;

FIG. 32 is a bottom view of the alligator cover of FIG. 31;

FIG. 33 is a front view of an IV pole covered to look like a palm tree;

FIG. 34 is a front view of a crutch covered to look like a flamingo;

FIG. 35 is a side view of a wheel chair covered to look like a throne;

FIG. 36 is a top view of a blood pressure cuff covered by a depiction of a starfish;

FIG. 37 is a bottom view of the embodiment of FIG. 36;

FIG. 38 s a top view of a blood pressure cuff covered by a depiction of a bear-like animal;

FIG. 39 is a bottom view of the embodiment of FIG. 38.

FIG. 40 is a top view of a blood pressure cuff covered by a depiction of a truck-like vehicle;

FIG. 41 is a side view of a covered ophthalmoscope showing a shroud that is a depiction of a snowman like structure;

FIG. 42 is a side view of an ophthalmoscope being placed into the cover of FIG. 41;

FIG. 43 is a side view of a covered ophthalmoscope showing a shroud that is a depiction of a rabbit-like structure;

FIG. 44 is a side view of an ophthalmoscope being placed into the cover of FIG. 43;

FIG. 45 is a side view of a covered ophthalmoscope showing a shroud that is a depiction of a turtle-like structure;

FIG. 46 is a side view of an ophthalmoscope being placed into the cover of FIG. 45;

FIG. 47 is a side view of a covered ophthalmoscope showing a shroud that is a depiction of a elephant-like structure;

FIG. 48 is a side view of a covered otoscope showing a shroud that is a depiction of a train-like structure;

FIG. 49 is a side view of an otoscope being placed into the cover of FIG. 48;

FIG. 50 is a side view of a covered otoscope showing a shroud that is a depiction of a penguin-like structure;

FIG. 51 is a front view of a shroud that is a depiction of a penguin-like structure;

FIG. 52 is a side view of an otoscope being placed into the cover of FIG. 50.

DETAILED DESCRIPTION OF THE INVENTION

The disclosed covers are unique in that they are not merely figurines or decorative ornaments that have just been attached to the equipment, but rather are covers that are specially designed and fitted to cover a unique piece of medical equipment such as a stethoscope, crutches, otoscope, syringe, blood pressure cuff, etc. These playful covers help make medical examinations and procedures easier and more enjoyable for the patient and health care provider while helping to provide more accurate clinical information. In the embodiments directed to use of medical equipment, such as crutches or wheelchair, the uniqueness of the cover adds some fun while removing some of the intimidation of the equipment.

The following is a description of examples medical equipment covers, referred to generally as a Pediapet, that have been designed to cover several common medical examining instruments. The Pediapets illustrated depict predominately flora and fauna, however other designs, such as sporting equipment, stereo or recording equipment, etc., can be used. When appropriate to the final appearance and to provide more of a stuffed animal feel or sculpted appearance, stuffing can be inserted between the double layers of fabric. These designs are used herein as examples and other designs will become apparent to those in the art which can be used for these and other medical instruments and rehabilitation equipment. Other medical apparatus that is easily "converted" would be IV poles that look like coconut trees, with the IV as a "monkey" and the IV tube the monkey's tail. A pair of crutches could be covered to appear as a couple of tree trunks or flamingos, while a wheelchair can be covered to appear as a throne or some type of vehicle. Most any object can become a Pediapet as long as it has the overall exterior configuration of the medical apparatus. For example, it would be difficult to incorporate a ground hog onto a crutch. The physical structure of the crutch is such that it requires a long, relatively thin Pediapet, such as the flamingo or a monument. Conversely, the wheelchair would lend itself to the Lincoln monument, but would not make an especially good bird. Items of clothing can also be incorporated into the Pediapet design, such as the tie described hereinafter.

Cartoon characters especially lend themselves to becoming a Pediapet. Not only are they easy to reproduce as a three dimensional character, but they represent a certain level of familiarity, especially children. Other examples will become obvious to someone skilled in the art in conjunction with the instant disclosure.

Stethoscope

The stethoscope 10, illustrated in FIG. 1, is a listening equipment used to amplify sounds originating from within a living body. Its design consists of a head 12, comprising a bell and diaphragm, a flexible connective tube 14 of varying length to conduct sound from the head 12 of the stethoscope 10 to the headset 16, and a headset 16 which conducts sound from the flexible connective tube 14 to the listener's ears. The headset 16 consists of two metal tubes connected at a "Y" spring joint. Soft ear pieces 20 are connected to the end of each metal tube.

The Pediapet is uniquely designed to fit the contours and shape of the stethoscope 10 without hindering its function and utility. FIGS. 2, 3, 4 and 5 illustrate examples of the shape of the covers which can be applicable. The elephant 21, illustrated in FIG. 2, is ideal for use with the stethoscope 10 as the trunk shaped sleeve 22 of the elephant 21 provides a natural cover for the connective tube 14 of the stethoscope 10. The ears and head, forming the body 24 of the cover also provide for an optimal aesthetic flow along the widest part of the headset 16. Due to its applicability, the attachment methods described herein will be directed to the elephant 21, however the various methods for attachment described hereinafter can be incorporated with any Pediapet embodiment.

In FIG. 3 a giraffe 30 is used to cover the stethoscope 10, with the head extending along one of the connective tubes 14 and the tail extending partially along the other tube 14. The legs of the giraffe 30 are, as with all 4 legged animals, "consolidated" into one "leg" to fit with the configuration of the stethoscope 10. In FIG. 4 the cover is a snug fitting cover 36 which can represent a tree branch or other inanimate object. One or more small animals 38 are then attached, either permanently or removably, to the cover 36. The removable animal 38 is advantageous in that it can be given to the patient to play with during the examination. In FIG. 5 the stethoscope 10 is covered with a cover resembling a neck tie 32 which widens along the length and then comes to a taper at the end. For aesthetics the necktie 32 is manufactured to appear as though it has a knot at the neck. In the optimum embodiment, the necktie 32 is affixed to the stethoscope mid-bar 18 through use of hook and loop material 33 or other means known in the art. The tie 32 is attached to the connective tube 14 through use of tabs 34.

In its ideal form, the instrument cover consists of a soft sleeve into which the above mentioned parts of the stethoscope 10 can be inserted. The sleeve is designed to conform to the shape of the stethoscope so that part of the sleeve fits around the listening tube and head of the stethoscope, and part of the sleeve fits around the headset. The sleeve is made of a single and/or double layer of fabric that surrounds part or the entirety of the instrument. Different amounts of stuffing are placed between the double layer of fabric to further define the desired appearance of the animal or object being represented. Those parts of the cover that are stuffed can be stuffed either all the way around the circumference of the sleeve or partially around the circumference enabling a variation in how flat the stethoscope rests against the user.

Using the elephant of FIG. 2 as an example, the portion of the sleeve 22 containing the connective tube 14 and head 12 of the stethoscope 10 is manufactured with sufficient width to allow the diaphragm portion of the head 12 to pass through the length of the sleeve 22 to the listening end open end. Since the width of the diaphragm varies from one brand of stethoscope to another, the inner diameter of this part of the sleeve must is at least 3–6 cm.

To prevent interference with the acoustics, it is critical that in all embodiments the end of the sleeve has an opening with a sufficient size to allow the stethoscope head to be exposed, allowing direct contact with the patient. More detailed examples of the ratio between the sleeve and the head 12 of the stethoscope are illustrated in FIGS. 9–12. In the embodiment of FIG. 10, the head 12 is always exposed through an opening at the end of the sleeve 42 and is always directly accessible. In the embodiment illustrated in FIG. 9, the sleeve 45 is longer than the length of the connective tube 14 and extends over the head 12. Therefore, the head 12 is not exposed until the sleeve 45 is pulled back to reveal the manufactured opening 44. Alternatively, the length of the sleeve can be less than the length of the connective tube and the head enclosed by a swatch of fabric folded over and secured by a snap, hook and loop material, etc. Additionally, any of the embodiments herein can have a closure system, such as hook and loop material. In the embodiment of FIG. 11 the opening 48 is placed along the length of the sleeve 46 proximate the head 12. To access the head 12, the head 12 is pulled through the opening 48 and the sleeve 46 pulled to one side. Since the surface area of the head 12 varies from one instrument to another the openings disclosed must be at least about 3–6 cm in diameter. In the design of FIG. 12, the open end 52 of the sleeve 50 is separated at approximately the middle, by a stirrup 54 of cloth or other material, which allows both the bell and diaphragm to be exposed simultaneously. The diameter of the openings are made wide enough for the entire surface of the bell and diaphragm to make contact with the patient.

In FIGS. 6, 7 and 8, the back of the elephant 21 illustrates the various methods of connecting the cover and the stethoscope 10. In FIG. 6 the elephant 70 has a slit 76 which allows the connective tube 14 to be enclosed within the trunk 78. The slit 76 must be at least 5–7 cm in width to allow the diaphragm of the head and the neck of the headset to pass into the sleeve 78. In this, as well as other embodiments wherein the connective tube 14 is placed within the sleeve, the sleeve must be of double layers of material, there requiring an increase in the outer dimensions of the sleeve. The headset 16 is maintained in position at the back of the cover body 72 through use of tabs 74. These tabs 74 can be snaps, hook and loop, or other connective means which enables the stethoscope 10 to be removed from the cover. The tabs 74 are placed not only to prevent the body 72 of the cover from flopping forward but should provide sufficient stability to prevent a child from easily dislodging the body 72 from the headset 16. In FIG. 7 the stethoscope 10 is affixed to the back of the body 82 and sleeve 88 of the elephant 80 through the use of tabs 84 as noted above. In this embodiment, however, the connective tube 14 does not slide into the sleeve 88, but rather lies adjacent the exterior of the sleeve 88. The connective tube 14 is retained adjacent the sleeve 88 through use of tabs 84 placed along the length.

In FIG. 8 the body 90 is designed to receive the stethoscope 10 within the full sleeve 94 formed from the fabric layers. The closure line 92 is designed to open to receive the headset 16 and connective tube 14 and then close, securing the stethoscope 10. The closure line 92 can be any closure means, such hook and loop, zipper, snaps, which can be repeatedly opened and closed. Since the headset is forked like a wishbone, the full sleeve 94 is also forked like a wishbone. The headset portion 98 of the sleeve 94 accommodates the metal tubes and, since the metal tubes are not as wide as the diaphragm of the stethoscope, the headset portion 98 only requires a minimum interior diameter of about 0.5 to 3 cm. Each end of the wishbone corresponds to the metal headset tubes and has an opening at the end, at least 0.5 cm, to permit the earpieces to pass through. In this embodiment, the closure line 92 opens to accommodate the connective tube, therefore enabling the diameter of the connective tube portion 96 to approximately equal to the headset portion 98. In embodiments where the closure line 92 only opens to accommodate the headset 16, the connective tube portion 96 must have an interior diameter sufficient to accommodate the head 12.

It must be noted that when attaching the stethoscope 10 to the back of any of the Pediapets, the need to expand the headsets 16 to accommodate the user must be taken into account. This becomes more critical as the Pediapet is placed closer to the ear pieces 20 and care must be taken to properly position the headsets 16 at the time of making the patterns. Since the item portrayed should be expanded fully during use, the tabs 34 or closure line 92 are positioned to maintain the headsets 16 in an "in use" position, causing the Pediapet to be slightly folded when in the closed positions illustrated in FIG. 1. The Pediapet can also be placed lower on the headsets 16, closer to the mid-bar 18, allowing for the required headset 16 flexibility to be above the restraints created by either the tabs 34 or the closure line 92.

An alternative method of inserting the stethoscope is to have the head and flexible listening tube pass into the instrument cover from an opening in the sleeve corresponding to the neck of the headset much in the same way that a foot would pass into a sock. With this construction a fastening equipment is designed to pass over the neck of the headset and latch the sleeve in place; this prevents the sleeve from sliding off the end of the instrument. Other designs contain a combination of the above mentioned insertion options. These designs allow for some parts of the stethoscope to slide into the sleeve while other parts of the stethoscope have the sleeve wrapped around it.

The decorative covers for the stethoscope are not limited to the sleeve design. The covers are also manufactured to cover just the front of the stethoscope. Like the sleeve design, these covers are specifically designed to follow the contour of the stethoscope and allow for complete function and utility of the instrument. The covers that attach to the front of the stethoscope consist of a couple layers of fabric or other manufactured material that are cut out, sewn together, and stuffed to look like an animal or some other familiar object. The cover is then secured to the stethoscope with fastening devices specially designed to wrap around the head, the flexible listening tube, the neck of the headset, and/or the metal headset tubes of the stethoscope to prevent it from falling off.

In the event sporting equipment is preferred over animals, the stethoscope can be designed as a golf bag containing golf clubs. The ear tubes would be two of the golf clubs while the base tube would be "hidden" in the golf bag. Decorative material can also be added to the Pediapet cover that aids in the artistic representation of the object or animal the cover represents.

Otoscope

The otoscope 100, illustrated in FIGS. 13 and 14, is a medical instrument principally used to examine a patient's ears, nose, throat, and sinuses. It consists of a handle 126 that can contain a power source and a detachable head 108 that houses an illumination source and optic pieces 104 and provides a place for the attachment of a speculum 106. The handle 126 and head 108 attach at the neck of the otoscope 100. Portable otoscopes 100 are turned off and on by a button and rotating cuff 102 located at the junction of the handle 126 and head 108 of the otoscope. This cuff 102 also controls the brightness of the light.

Some otoscopes turn on automatically when they are removed from a holding rack that is usually mounted on a wall. These otoscopes are plugged into a power source and the electrical cord runs from the holding rack to the bottom of the handle of the otoscope. Still other otoscopes sit in a charging rack that makes contact with the instrument at the bottom of the handle. These otoscopes do not have a cord attached to them.

There are different sized otoscopes and there are slight variations in their shape depending on the company producing the instrument. This description of the Pediapet pertains to use with a standard sized portable otoscope. However, scaled down versions, and slight variations are made to the design of the Pediapet to cover other instrument sizes and accommodate mounting and recharging devices.

The Pediapet is designed to cover the handle 126 and/or the head 108 of the otoscope 100 while enabling full function and utility of the instrument. In its ideal form the otoscope Pediapet consists of a hollow sleeve 120 that is sealed at one end, such as illustrated in FIGS. 15-21. The sleeve 120 of the Pediapet is approximately 17 cm long, but varies slightly with model of the otoscope and the design of the animal or object it represents. The Pediapet is made to enable the otoscope 100 to slide in handle 126 first through an open end or slit 124 in the sleeve of the Pediapet.

This covers the handle 126 and, in some cases, part of the neck of the instrument. A specially designed hood 122 is attached to the sleeve and is pulled up over the head 108 of the otoscope. The hood 122, in the illustrated embodiment, is approximately 5.0 cm in length to enable the hood 122 to be easily placed over the otoscope head 108. In some cases, depending on size of the instrument and design of the Pediapet, the hood can also be an extension of the sleeve. Two holes are made in the hood 122 to permit examination of the patient. The viewer hole 128 is closest to the examiner's eye and generally has a periphery of at least about 2.5×3.0 cm and enables the viewer to look through the optic lens. The speculum hole 130 is opposite the first and is at least 0.5 cm in diameter to accommodate the speculum 106 attached to the head of the otoscope 100. The hood 122 must be designed so that if it does extend beyond the length of the speculum 106 or beyond the viewing lens 104, it does not block the user's vision. For the otoscope 100 illustrated, this is 5.5 cm from one opening to the other.

The sleeve 120 is made of a single and/or double layer of material. The double layer of material allows the Pediapet to be stuffed to give form and structure to the animal or object the Pediapet represents. The structure is particularly important for the hood 122 of the Pediapet that covers the head 102 of the instrument so that it does not slip down in front of the optic lens 104 or speculum 106 opening during use. A slit 124 in the sleeve corresponding to the location of the rotating cuff allows for access to the on/off/brightness switch 102. This slit 124 also allows the office otoscopes 140 to be placed back in its holding rack 142 as illustrated in FIG. 19. For those otoscopes 150 that fit into a recharging rack 152, as illustrated in FIGS. 20 and 21, slight alterations are made to the closed end of the sleeve 154. Since contact needs to be made at the base 156 of the handle, either a small hole 158 is made in the closed end of the sleeve 154 to allow for contact, or the closed end is designed so that it can be opened with a strip of Velcro, a snap, a zipper, or other fastening equipment. Similar alterations are made for those Pediapets 170, as illustrated in FIG. 17, that cover otoscopes 174 that are plugged into an electrical cord 172. Since the electrical cord 172 attaches to the base of the handle, a hole or opening 176 is manufactured in the Pediapet 170 sleeve as described above.

For the standard sized otoscope the sleeve is at least 3.0 cm wide to allow for the handle to slide through the sleeve. Areas that need to allow passage of the head through the sleeve are at least 5.0 cm wide.

Some variations in the Pediapet are designed to just cover the handle 126 of the otoscope. These Pediapets correspond to the description of the sleeve above. Others are designed to cover just the head 108 of the otoscope and correspond to the description of the hood above. There are several alternative ways in which the otoscope sleeve and hood can be attached in the event they are not stitched together. These can include snaps, hook and loop material, or other methods that permit the insertion and removal of the otoscope. Alternatively, the hood can be left unattached and simply slid over the otoscope head. This would be applicable when using a cover representing a baseball bat, wherein the handle of the bat would be the handle of the otoscope and easily closed through the use of hook and loop material. A viewing channel would be cut through the bat to coordinate with the viewing lens, as described heretofore. Additional decorative material can be attached to the Pediapet cover to aid in the artistic representation of the object or animal the cover/Pediapet represents. It should also be noted that the dimensions disclosed herein are for example purposes and will vary depending upon the otoscope and Pediapet design.

Ophthalmoscope

The ophthalmoscope 202 is a medical instrument used to examine a patients' eyes. It consists of a handle 232 that may contain a power source and a detachable head 230 which houses an illumination source and optic pieces. The handle 232 of the ophthalmoscope is often times interchangeable with the handle of the otoscope. The handle 232 and head 230 attach at the neck of the ophthalmoscope. Portable ophthalmoscopes are turned off and on by a button and rotating cuff 228 located at the junction of the handle and head of the ophthalmoscope. This cuff 228 also controls the brightness of the light. Some ophthalmoscopes turn on automatically when they are removed from a holding rack that is usually mounted on a wall. These ophthalmoscopes are plugged into a power source and the electrical cord runs from the holding rack to the bottom of the handle of the ophthalmoscope. Still other ophthalmoscopes sit in a charging rack that makes contact with the instrument at the bottom of the handle. These ophthalmoscopes do not have a cord attached to them.

The design of the ophthalmoscope Pediapet is very similar to that of the otoscope Pediapet. There are different sized ophthalmoscopes and slight variations in their shape depending on the company producing the model. This description of the Pediapet is designed to cover the standard sized portable ophthalmoscope. However, scaled down versions, and slight variations are made to the design of the Pediapet to cover other instrument sizes.

The Pediapet is designed to cover the handle 232 and/or the head 230 of the ophthalmoscope 202 while allowing for full function and utility of the instrument. In its ideal form the ophthalmoscope Pediapet 200 consists of a hollow sleeve 210, within the Pediapet 200 body, that is sealed at one end. The sleeve of the Pediapet is approximately 17 cm long, but varies slightly with the design of the animal or object it represents. The Pediapet illustrated in FIGS. 23–29 is made so that the ophthalmoscope slides in handle first through an open end or slit in the sleeve 208 of the Pediapet 200. This covers the handle 202 and in some cases part of the neck of the instrument. A specially designed hood 206 is attached to the sleeve and is pulled up over the head 204 of the ophthalmoscope. The hood is approximately 7.0 cm in length to fit over the head of the instrument. In some cases the hood is an extension of the sleeve 210. Two holes, viewing hole 212 and lens hole 214 are made in the hood 206 to permit the user to examine the patient. In order to ensure unimpaired access through the optic lens, the viewing hole 212 must measure at least about 1.0×1.0 cm. The lens hole 214, directly opposite, is at least 1.0×1.5 cm in diameter. These holes are connected and aligned to permit an unobstructed view of the patient's eye.

The sleeve 210 is made of single and/or double layers of material, with the double layer of material allows the Pediapet to be stuffed. This helps give form and structure to the animal or object the Pediapet represents. The structure is particularly important in preventing the hood 206 of the Pediapet 200 covering the head 204, from slipping down in front of the optic lens during use. The slit 208 in the sleeve 210 preferable serves to permit access to the on/off/brightness switch as well as enable easy insertion of the ophthalmoscope 200. This slit 208 also allows the office ophthalmoscopes 250 of FIG. 18, to be placed back in its holding rack 252. Additional slit(s) 220, are made in the side of the hood 206 to allow access to a focusing knob 220, and in the front of the hood 212 to access an aperture wheel and the switch to change light color. Variations in the design of the head cover must maintain the focusing knob, aperture and light switch sufficiently exposed to enable use.

For those ophthalmoscopes 270, as illustrated in FIGS. 27 and 28, that fit into a recharging rack 272, slight alterations are made to the closed end of the sleeve 274. Since contact needs to be made at the base of the handle 276, either a small hole 278 is made in the closed end of the sleeve 274 to allow for contact, or the closed end is designed so that it can be opened with a strip of Velcro, a snap, a zipper, or other fastening equipment. Similar alterations are made for those Pediapets 290 that cover ophthalmoscopes using an electrical cord 292, as illustrated in FIG. 25. Since the electrical cord 292 attaches to the base of the handle, a hole 294 or opening is manufactured in the Pediapet sleeve as described above.

For the standard sized ophthalmoscope the sleeve is at least about 3.0 cm wide to allow for the handle to slide through the sleeve. Areas that need to allow passage of the head through the sleeve are at least about 4.0 cm wide. These dimensions will vary dependent upon the make of the ophthalmoscope and design of the pet.

Some variations in the Pediapet are designed to only cover either the handle or head of the ophthalmoscope. These Pediapets correspond to the description of the sleeve or hood above. As with the Pediapet for the otoscope, there are several alternative ways in which the ophthalmoscope can be inserted into the sleeve of the ophthalmoscope Pediapet and are described heretofore. As with the otoscope, additional decorative material can be attached to aid in the artistic representation of the object or animal.

Blood Pressure Cuff

The blood pressure cuff, as illustrated in FIG. 30, is used to measure a patient's systolic and diastolic blood pressure. It consists of a cuff that fastens around a patient's limb, a rubber bladder that is inflated to expand the cuff, a rubber tube of variable length that connects the bladder to an inflation bulb, and a gauge. The gauge can be mounted to the cuff, to the inflation bulb, or on the wall. Still other gauges hang freely from the cuff by means of a second rubber tube.

In its ideal form, the blood pressure cuff Pediapet as illustrated in FIGS. 31 and 32, will consist of a sleeve 502 that looks like an animal and/or other familiar object, such as an alligator 500. The blood pressure Pediapet cover functions as a sleeve 502 to encircle a patient's arm or leg, and is designed to contain the inflatable bladder 504 of the blood pressure cuff 506. The dimensions of the sleeve 502 are approximately that of standard adult or pediatric blood pressure cuffs 506, 14×55 cm and 11×35 cm respectively. The sleeve 502 is constructed from a double layer of fabric or other flexible material. On the side of the Pediapet contacting the patient, is a pocket 508 into which the inflatable bladder 504 is inserted. Starting at one inside edge of the sleeve 502, the pocket 508 is approximately one third to one half of the total sleeve area. The pocket measures about 29 cm long and 14 cm wide for the adult size, and 20 cm long and 10.5 cm wide for the pediatric size. To allow the rubber tube, or tubes, to connect to the bladder, a hole 510 is made in the long edge of the pocket. This hole 510 is approximately 1–2 cm in length and is located approximately 4–7 cm in from the short, outside edge of the pocket. In the optimum embodiment, the tube is run through one of the Pediapet's legs.

Hook and loop material is used to secure the Pediapet around the patient's limb. The hook portion 512 is located on the outside of the Pediapet, and measures approximately 11×10.5 cm for the adult Pediapet, and 5×8 cm for the pediatric Pediapet. On the inside of the Pediapet, a large section of loop material 514 is attached to the end opposite the end of the loop material 512. This section of loop material 514 measures about 25.5×10.5 cm for the adult size and 15×6.5 for the child size. It should be noted that the foregoing dimensions are approximate and are provided herein as examples and ratios only and not intended to limit the scope of the invention.

The outside of the blood pressure Pediapet can have an extra piece or pieces of fabric cut and sewn into the shape of the object and/or animal that the Pediapet is designed to portray. Stuffing can be contained between the layers of fabric to aid in giving the Pediapet the appearance of the animal and/or objects.

The hook material 512 either is left exposed, or is minimally covered by a flat piece of fabric. If one part of the Pediapet overlays the hook material 512, it is designed so that it may be lifted out of the way, folded back and secured, or removed when the Pediapet is being used to measure blood pressure. A stuffed head, legs, tail, tree branches or other objects may extend beyond the minimum measurements of the sleeve in order to aid in the portrayal of the object. The flexible rubber tube or tubes may fit through one of these extensions forming a small sleeve through which the tube may be threaded.

In an alternative design, the Pediapet is manufactured as a cover to fit over a preexisting blood pressure cuff. In this design, the existing cuff slides into a sleeve that is designed to look like part of an object and/or animal. The Pediapet cover is then secured around the cuff by means of a zipper, Velcro, snaps, tie strings, or other fastening equipment. The part of the sleeve coming in contact with the patient, in general, consists of one layer of fabric and does not have any stuffing in between it and the cuff. The outside part of the sleeve consists of one to several layers of fabric and contains variable amounts of stuffing to aid in the representation of the object and/or animal the sleeve portrays. Additional decorative material may be attached to the outside of the sleeve to also aid in portrayal. A hole is made in the bottom edge of the cover corresponding to the entrance of the flexible rubber tube into the bladder of the cuff. As with the first design, a stuffed head, legs, tail, tree branches or other objects may extend beyond the minimum measurements of the cover in order to aid in the portrayal of the object. Often, these parts of the Pediapet contain stuffing. The flexible rubber tube or tubes may fit through one of these extensions forming a small sleeve through which the tube may be threaded.

Iv Pole

IV poles can be quite intimidating for children and adults as they are generally used in hospital settings and require the use of a needle. To "soften" the appearance, the IV pole 600, illustrated in FIG. 33, is covered with a coconut tree trunk 602 with fonts at the top of the trunk 602. The support pole 604 in this Figure is not covered, however, this is dependent upon the Pediapet design. A monkey 610 containing the bag of IV fluid 606 is hanging off the support pole 604. The monkey 610, or other figure, must be dimensioned to permit the standard IV bag, or other medical apparatuses, to be hung in the standard fashion so as to permit the apparatus to function. If the bag 606 is merely placed into the stomach of a stuffed animal, it would drop and hamper the fluid flow. The bag 606 can be either connected to the monkey's head or an access hole can be provided in the back of the monkey to accept the standard hanging element associated with the IV. The preferred method will become apparent to those skilled in the art and will be dependent upon the apparatus and Pediapet design. In this Figure, the tail 608 of the monkey 610 is used as the IV tube. This can be covered, however for medical safety it may be desirable to leave the tail uncovered. The tree trunk 602 is manufactured from two pieces of material with stuffing in between to simulate the tree trunk. The tree fonts can be manufactured from green felt or other appropriate material. The trunk 602 can be secured, once wrapped around the IV pole 600, through use of hooks, snaps, hook and loop material, etc. The dimensioning of the trunk 600 must be such that it does not interfere with the standard functionality of the IV pole, i.e., the wheels must be free to move, it must continue to pass through doors, be lightweight, etc.

The IV pole can easily be covered to resemble any elongated item, such as a space ship, building or monument. For example, the IV pole could be the Empire State Building and the IV bag King Kong.

Crutches

Although crutches are not as intimidating as the majority of medical instruments, they still reflect an inability of the patient to function in their usual manner. To make using crutches more fun, Pediapets can be affixed to the crutch. In FIG. 34 a crutch has been covered with a flamingo 652. The flamingo 652 is a stuffed figure that is attached to the crutch 650 through use of tabs, etc., as disclosed heretofore in relation to the stethoscope. Preferable the back of the flamingo 652 is below the hand grip 654 to avoid interfering with the patient's use. This, however, is dependent upon the design and some designs, such as a knurled tree, can incorporate the hand grip 654 into the design.

Wheelchair

In FIG. 35 the wheelchair 670 is covered to appear as a throne by placing a throne cover 672 over the chair 670. The throne cover 672 must be dimensioned to securely fit over the chair 670 without interfering with the wheels 674. The cover 672 should be stuffed to portray a throne while accommodating all parts of the wheelchair 670. A strap can, if necessary, be provided to run under the seat of the wheelchair 670 to maintain the preferred snugness as well as keep the cover away from the wheels 674. The throne cover can also be an animal, such as a bear, or an object, such as a rocket seat, that is stuffed to provide the appropriate appearance.

The materials used for the foregoing Pediapets must be appropriate to the end use, i.e. elephant trunks must be flexible, as should the "tree" branches. All materials are preferably easy to clean and allergy free. The material must also have the ability to hold up under repeated washings. At least some level of water repellency is additionally beneficial. Preferably the materials chosen are soft, providing the comfort associated with stuffed animals, although, again, this would be dependent upon the animal or object portrayed. The material chosen for manufacture will determine the method of construction, i.e. fabric is sewn or melt-glued or other methods applicable to the chosen fabric, plastics can be molded or extruded.

ADDITIONAL EMBODIMENTS

FIG. 36 shows another embodiment in which a starfish is used in place of the alligator of FIG. 31. The starfish embodiment of FIG. 37 corresponds to the illustration of FIG. 32. Other embodiments can include other relatively flat bodied animals in addition to alligators and starfish. Fish are particularly suitable for encapsulating the blood pressure cuff. Among the fish that can be used are any of various stingrays of the family Dasyatidae, having a whiplike tail. It is also called stingaree. Additionally the animal can be a Manta. Manta is any of several rays of the family Mobulidae, inhabiting tropical and subtropical seas and having a large flattened body, winglike pectoral fins, a whiplike tail, and two hornlike fins that project forward from the head. In this sense, also called devilfish, manta ray, sea devil.

FIGS. 38 and 39 illustrate a bear like animal, in particular a teddy bear or panda. The bear or bear like animal is preferably used in an essentially flat version with the cuff extending from one paw to the other.

Other animals include the ferret, a weasel like, usually albino mammal. Other weasel like animals include the mink, any of various semiaquatic carnivores of the genus Mustela, especially M. vison of North America, resembling the weasel and having short ears, a pointed snout, short legs, and partly webbed toes.

FIG. 40 shows a different variation in which the blood pressure cuff is enclosed within a decorative replica of a truck. As in the case of the bear, the cover is formed from two layers of fabric and is essentially a flat cover.

FIGS. 41 and 42 illustrate a snow man cover for an ophthalmoscope. FIG. 42 shows the ophthalmoscope being inserted into the snow man cover. Similarly, FIGS. 43 and 44 illustrate a rabbit cover employed in a manner similar to the embodiments of FIGS. 41 and 42, as well as the embodiments of FIGS. 23 through 29.

FIGS. 45 and 46 illustrate turtle embodiments while FIG. 47 illustrates an elephant embodiment. It should be noted that the illustration of FIG. 47 corresponds to the embodiment of FIG. 28.

FIGS. 48 and 49 illustrate otoscope covers in the form of a train. Similarly, the cover can be in the form of a truck FIGS. 50, 51 and 52 illustrate a penguin type of otoscope cover.

It should be noted that the type of objects previously illustrated as covers for the otoscope can also be used for the ophthalmoscope and those illustrated for the ophthalmoscope can also be used for the otoscope.

In the case of the elephant, the truck can be used to enclose the speculum. With bird like animals, the beak can be used to enclose the speculum.

The goal of the Pediapet is to increase the comfort level of a patient during an examination and/or use of medical equipment. It is therefore important that the appearance of the product addresses this point. Although a number of materials can be used to make the foregoing, all materials should be appropriately chosen for the end use. It should also be noted that the illustrated Pediapets, as well as their dimensioning, are used as examples only. Further, the medical equipment disclosed herein are for examples only and are not intended to limit the scope of the invention. Those skilled in the art will be aware of alternate designs and appropriate dimensioning that will corresponding with the selected medical equipment.

What is claimed is:

1. The method of examining a patient, using a medical examination instrument for the examination of a body part,
    said instrument having a distal end and a proximal end and comprising a light source and a optical viewing element, said optical viewing element being at said instrument proximal end, comprising the step of inserting said medical instrument into said three dimensional representation of an object unrelated to a medical instrument,
    said object having an upper region, and said upper region having at least one opening, positioned said optical viewing element within said upper region, aligning said optical viewing element with an opening in upper region, and said viewing said body part through at least one opening in said upper region.

2. The method of claim 1, wherein said object is a three dimensional representation of an animal, said animal having a head region and said head region having an eye region and a region resembling an animal's mouth,
    Positioning said animal head region being proximate said instrument distal end, aligning said optical viewing element with an opening in animal head region, and viewing said patient body part through at least one opening in said head region.

3. A medical examination instrument for the examination of a body part, said instrument having a distal end and a proximal end and a three dimensional representation of an animal, said medical instrument being substantially within said three dimensional representation of a non-medical object.

4. The medical examination instrument of claim 3, said instrument further comprising a light source and a optical viewing element, said optical viewing element being at said instrument proximal end, said non-medical object being animal having a head region, said head region having an eye region and a region resembling an animal's mouth, said animal head region being proximate said instrument distal end, said optical viewing element being positioned within said head region such that a user can see through at least one opening in said head region.

5. The medical instrument of claim 4, wherein said optical viewing element is aligned with said eye region, whereby an optical light path is provided through said representation of an animal and though said medical instrument, said optical path being through said animal's mouth.

6. The medical instrument of claim 4, wherein said optical viewing element is aligned with said eye region, whereby an optical light path is provided through said representation of an animal and though said medical instrument, said optical path being through said animal's eye region.

7. The medical instrument of claim 4, wherein said optical viewing element is aligned with said eye region, whereby an optical light path is provided through said representation of an animal and though said medical instrument, wherein said optical viewing element is a magnifying lens.

8. The medical instrument of claim 4, wherein said optical viewing element is aligned with said eye region, whereby an optical light path is provided through said representation of an animal and though said medical instrument, wherein said instrument is an otoscope.

9. The medical instrument of claim 4, wherein said optical viewing element is aligned with said eye region, whereby an optical light path is provided through said representation of an animal and though said medical instrument, wherein said instrument is an ophthalmoscope.

10. The medical instrument of claim 4, wherein said representation of an animal is formed of a molded, self supporting material.

11. The medical instrument of claim 4, wherein said representation of an animal is formed from a fabric and is supported by said medical instrument.

12. The medical instrument of claim 3, said instrument being a stethoscope having
    a pair of ear members, a distal end and a pair of proximal ends,
    said pair of ear members being at said proximal ends of said stethoscope, a diaphragm member at the distal end of said stethoscope,
    an elongated sound transmitting member between said ear members and said diaphragm member,
    said non-medical object being a necktie member,
    said necktie member having a proximal end and a distal end and substantially covering said elongated sound transmitting member, and having a tied section at said proximal end
    said necktie proximal end at a position spaced from said ear members and said necktie distal end being proximate said diaphragm member,
    said necktie proximal end being proximate the neck of the user of said stethoscope when said stethoscope is on said user, and said necktie distal end being proximate said stethoscope distal end, said necktie being affixed to said sound transmitting member and having a dimension sufficient to substantially entirely cover and hide said sound transmitting member.

13. The medical instrument of claim 3, wherein said medical instrument is a blood pressure cuff comprising a pressurized air delivery member, a cuff member, said cuff member having an inflatable bladder, said bladder being in air communication with said air delivery member, said cuff member having
- a first substantially planar side and a second substantially planar side,
- first attachment means on said first side for attachment to second attachment means on said second side, said three dimensional representation of a non-medical device substantially covering said cuff member but not said first attachment means or said second attachment means, and being secured to said cuff member.

14. The medical instrument of claim 13, wherein one of said first attachment means and said second attachment means is a hook member and the other is a loop member.

15. The medical instrument of claim 13, wherein said three dimensional representation is a fish.

16. The medical instrument of claim 13, wherein said three dimensional representation is an alligator.

17. The medical instrument of claim 13, wherein said three dimensional representation is a representation of a weasel-like animal.

18. The medical instrument of claim 17, wherein said weasel-like animal is a mink or a ferret.

* * * * *